US011911000B2

(12) United States Patent
Culman et al.

(10) Patent No.: US 11,911,000 B2
(45) Date of Patent: *Feb. 27, 2024

(54) ENDOSCOPE INCLUDING A PLURALITY OF INDIVIDUALLY TESTABLE SUBASSEMBLIES

(71) Applicant: INTUITIVE SURGICAL OPERATIONS, INC., Sunnyvale, CA (US)

(72) Inventors: William Jason Culman, Santa Cruz, CA (US); Jaime G. Blackstad, San Jose, CA (US); Dominique D. Brichard, San Jose, CA (US); Peter M. Herzlinger, Saratoga, CA (US); Willard Curtis Lomax, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/486,201

(22) Filed: Sep. 27, 2021

(65) Prior Publication Data
US 2022/0071475 A1 Mar. 10, 2022

Related U.S. Application Data

(63) Continuation of application No. 16/317,696, filed as application No. PCT/US2017/032082 on May 11, 2017, now Pat. No. 11,141,046.
(Continued)

(51) Int. Cl.
*A61B 1/00* (2006.01)
*G01M 3/26* (2006.01)
(Continued)

(52) U.S. Cl.
CPC .............. *A61B 1/0011* (2013.01); *G01M 3/26* (2013.01); *G01N 27/041* (2013.01);
(Continued)

(58) Field of Classification Search
CPC ... A61B 1/0011; A61B 1/00057; A61B 1/051; A61B 1/07; A61B 1/00114; G01M 3/26;
(Continued)

(56) References Cited

U.S. PATENT DOCUMENTS 3,943,271 A * 3/1976 Bahder .................. H02G 15/04
174/23 R
4,130,450 A * 12/1978 Bahder .................. H01B 7/285
174/106 SC
(Continued)

FOREIGN PATENT DOCUMENTS

CN 1954768 A 5/2007
CN 201149779 Y 11/2008
(Continued)

OTHER PUBLICATIONS

Office Action dated Jul. 4, 2022 for European Application No. EP17828105.1 filed May 8, 2017.
(Continued)

*Primary Examiner* — Tung T Vo
(74) *Attorney, Agent, or Firm* — Meunier Carlin & Curfman LLC

(57) ABSTRACT

An endoscope includes a first subassembly, a second subassembly, a third subassembly, and a fourth subassembly, which are sequentially assembled and tested in making the endoscope. The first subassembly includes a pressure-sealed electrical cable connected to an image capture unit. The second subassembly includes the first subassembly, a shell, a light pipe, and a lid. The third subassembly includes the second subassembly, a central tube, and a flange. The fourth
(Continued)

subassembly includes the third subassembly, a base, a shaft, and optionally an articulating assembly.

17 Claims, 10 Drawing Sheets

Related U.S. Application Data

(60) Provisional application No. 62/362,187, filed on Jul. 14, 2016.

(51) Int. Cl.
*H04N 23/54* (2023.01)
*G01N 27/04* (2006.01)
*H04N 23/55* (2023.01)
*H04N 23/50* (2023.01)

(52) U.S. Cl.
CPC ............. *H04N 23/54* (2023.01); *H04N 23/55* (2023.01); *A61B 1/00057* (2013.01); *H04N 23/555* (2023.01)

(58) Field of Classification Search
CPC G01M 3/3263; G01M 3/3272; G01N 27/041; H04N 5/2253; H04N 5/2254; H04N 2005/2255; G02B 23/2415; G02B 23/2423
USPC .......................................................... 348/76
See application file for complete search history.

(56) References Cited

U.S. PATENT DOCUMENTS

| | | | | |
|---|---|---|---|---|
| 4,360,704 | A * | 11/1982 | Madry | H01B 9/02 174/23 R |
| 4,449,013 | A * | 5/1984 | Garshick | H01B 7/226 174/109 |
| 4,874,364 | A | 10/1989 | Morris et al. | |
| 4,963,695 | A * | 10/1990 | Marciano-Agostinelli | B29C 48/06 156/48 |
| 5,010,209 | A * | 4/1991 | Marciano-Agostinelli | H01B 9/02 174/23 C |
| 5,148,864 | A * | 9/1992 | Willis | E21B 33/0407 166/65.1 |
| 5,158,086 | A | 10/1992 | Brown et al. | |
| 5,448,864 | A | 9/1995 | Rosamond | |
| 5,547,456 | A | 8/1996 | Strobl et al. | |
| 5,858,667 | A | 1/1999 | Dertinger et al. | |
| 5,868,667 | A | 2/1999 | Lin et al. | |
| 5,868,687 | A | 2/1999 | Tedesco | |
| 6,398,776 | B1 | 6/2002 | Sekino et al. | |
| 6,412,334 | B1 | 7/2002 | Kral et al. | |
| 6,547,721 | B1 | 4/2003 | Higuma et al. | |
| 6,547,724 | B1 | 4/2003 | Soble et al. | |
| 6,671,581 | B2 | 12/2003 | Niemeyer et al. | |
| 6,871,581 | B2 | 3/2005 | Suzuki | |
| 7,030,904 | B2 * | 4/2006 | Adair | A61B 1/00135 348/E3.019 |
| 7,942,868 | B2 | 5/2011 | Cooper et al. | |
| 8,608,648 | B2 | 12/2013 | Banik et al. | |
| 9,060,678 | B2 | 6/2015 | Larkin et al. | |
| 10,799,303 | B2 | 10/2020 | Cooper et al. | |
| 11,141,046 | B2 | 10/2021 | Culman et al. | |
| 2001/0016679 | A1 | 8/2001 | Futatsugi et al. | |
| 2001/0025134 | A1 | 9/2001 | Bon et al. | |
| 2001/0032494 | A1 | 10/2001 | Greszler | |
| 2002/0062062 | A1 | 5/2002 | Belson et al. | |
| 2003/0036748 | A1 | 2/2003 | Cooper et al. | |
| 2003/0149339 | A1 * | 8/2003 | Ishibiki | A61B 1/05 600/160 |
| 2004/0139789 | A1 | 7/2004 | Masters | |
| 2004/0254566 | A1 * | 12/2004 | Plicchi | A61B 34/37 606/1 |
| 2005/0119527 | A1 | 6/2005 | Banik et al. | |
| 2005/0131279 | A1 | 6/2005 | Boulais et al. | |
| 2005/0245789 | A1 | 11/2005 | Smith et al. | |
| 2006/0025651 | A1 | 2/2006 | Adler et al. | |
| 2006/0074383 | A1 | 4/2006 | Boulais | |
| 2006/0178556 | A1 | 8/2006 | Hasser et al. | |
| 2006/0258855 | A1 | 11/2006 | Gasser et al. | |
| 2006/0258955 | A1 | 11/2006 | Hoffman et al. | |
| 2006/0259041 | A1 | 11/2006 | Hoffman et al. | |
| 2007/0049435 | A1 | 3/2007 | Jinno et al. | |
| 2008/0294007 | A1 | 11/2008 | Takada | |
| 2009/0076328 | A1 | 3/2009 | Root et al. | |
| 2009/0227842 | A1 | 9/2009 | Ando | |
| 2010/0201794 | A1 | 8/2010 | Kido et al. | |
| 2010/0261961 | A1 * | 10/2010 | Scott | A61B 1/00096 600/111 |
| 2011/0101068 | A1 | 5/2011 | Sonnenschein et al. | |
| 2011/0201883 | A1 | 8/2011 | Cooper et al. | |
| 2012/0206583 | A1 | 8/2012 | Hoshi et al. | |
| 2013/0027534 | A1 | 1/2013 | Kibayashi | |
| 2013/0102846 | A1 | 4/2013 | Sjostrom et al. | |
| 2014/0100425 | A1 | 4/2014 | Metras et al. | |
| 2014/0163664 | A1 * | 6/2014 | Goldsmith | A61B 17/0057 604/93.01 |
| 2014/0206936 | A1 | 7/2014 | Cooper et al. | |
| 2015/0032024 | A1 | 1/2015 | Furlong et al. | |
| 2015/0066002 | A1 | 3/2015 | Cooper et al. | |
| 2015/0075838 | A1 | 3/2015 | Buck et al. | |
| 2015/0083950 | A1 | 3/2015 | Okiyama | |
| 2015/0216396 | A1 | 8/2015 | Banik et al. | |
| 2015/0245763 | A1 | 9/2015 | Kido | |
| 2015/0313452 | A1 | 11/2015 | Hasser et al. | |
| 2015/0340133 | A1 | 11/2015 | Jungbauer et al. | |
| 2016/0095508 | A1 | 4/2016 | Terliuc et al. | |
| 2016/0266004 | A1 | 9/2016 | Van Nest et al. | |
| 2016/0309992 | A1 | 10/2016 | Stith et al. | |
| 2017/0056118 | A1 | 3/2017 | Cooper et al. | |
| 2017/0065156 | A1 | 3/2017 | Ariyoshi et al. | |
| 2017/0119470 | A1 | 5/2017 | Diamant et al. | |
| 2018/0309908 | A1 | 10/2018 | Matthison-Hansen et al. | |
| 2019/0290104 | A1 | 9/2019 | Culman et al. | |

FOREIGN PATENT DOCUMENTS

| | | |
|---|---|---|
| CN | 101849335 A | 9/2010 |
| CN | 103682931 A | 3/2014 |
| CN | 104620329 A | 5/2015 |
| CN | 104882688 A | 9/2015 |
| CN | 105193371 A | 12/2015 |
| CN | 105556620 A | 5/2016 |
| DE | 20214968 U1 | 2/2004 |
| EP | 2110069 A1 | 10/2009 |
| EP | 2716205 A1 | 4/2014 |
| ES | 1059427 U | 4/2005 |
| JP | H08304711 A | 11/1996 |
| JP | H10234649 A | 9/1998 |
| JP | H11309112 A | 11/1999 |
| JP | 2000189385 A | 7/2000 |
| JP | 2004000681 A | 1/2004 |
| JP | 2005204836 A | 8/2005 |
| JP | 2006521882 A | 9/2006 |
| JP | 2007037786 A | 2/2007 |
| JP | 2010538759 A | 12/2010 |
| JP | 2012089288 A | 5/2012 |
| JP | 2013226281 A | 11/2013 |
| WO | WO-02076290 A1 | 10/2002 |
| WO | WO-2004086957 A2 | 10/2004 |
| WO | WO-2007120353 A2 | 10/2007 |
| WO | WO-2013031388 A1 | 3/2013 |

OTHER PUBLICATIONS

Alphawire, "Understanding Shielded Cable," Mar. 29, 2013, Retrieved from the Internet : https://www.mouser.com/pdfdocs/alphawire-Understanding-ShieldedCable.pdf, pp. 1-6.

(56) References Cited

OTHER PUBLICATIONS

Extended European Search Report for Application No. EP17828105.1 dated Dec. 6, 2019, 7 pages.
Extended European Search Report for Application No. EP17828107.7 dated Feb. 4, 2020, 8 pages.
Fibertech Medical, "Are You Properly Leak Testing Your Flexible Endoscope?", 2006, 2 pages.
International Preliminary Report on Patentability for Application No. PCT/US2017/031592, dated Jan. 24, 2019, 9 pages.
International Preliminary Report on Patentability for Application No. PCT/US2017/032082, dated Jan. 24, 2019, 11 pages.
International Search Report and Written Opinion for Application No. PCT/US2017/031592, dated Aug. 8, 2017, 12 pages.
International Search Report and Written Opinion for Application No. PCT/US2017/032082, dated Aug. 1, 2017, 19 pages.
Office Action dated Apr. 6, 2021 for Japanese Application No. 20190500862 filed May 8, 2017, 08 pages.
Office Action dated Apr. 30, 2021 for Chinese Application No. 20178038760 filed May 11, 2017, 34 pages.
Peng, Wang, "Interpretation of Airworthiness Requirements for Transport Aircraft vol. 6 use Restriction Information and Electrical Wiring Interconnection System," Aviation Industry Press, Sep. 2013, 4 pages.
Second Office Action received in connection with Chinese Patent Application No. 201780042179.9, dated Jul. 21, 2021, 32 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Office Action for Chinese Application No. CN20178038760, dated Jun. 28, 2022, 43 pages.
Office action dated Jan. 5, 2022, for Application No. CN201780038760.3 filed May 11, 2017 with English Translation, 49 pages.
Extended European Search Report for Application No. EP23154336.4, dated May 12, 2023, 08 pages.
Extended European Search Report for Application No. EP22203967.9, dated Feb. 7, 2023, 08 pages.

\* cited by examiner

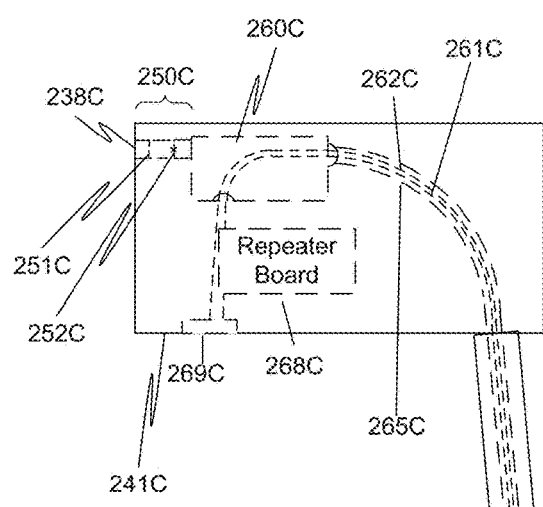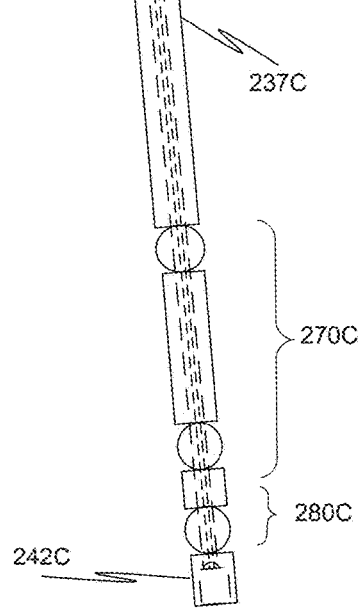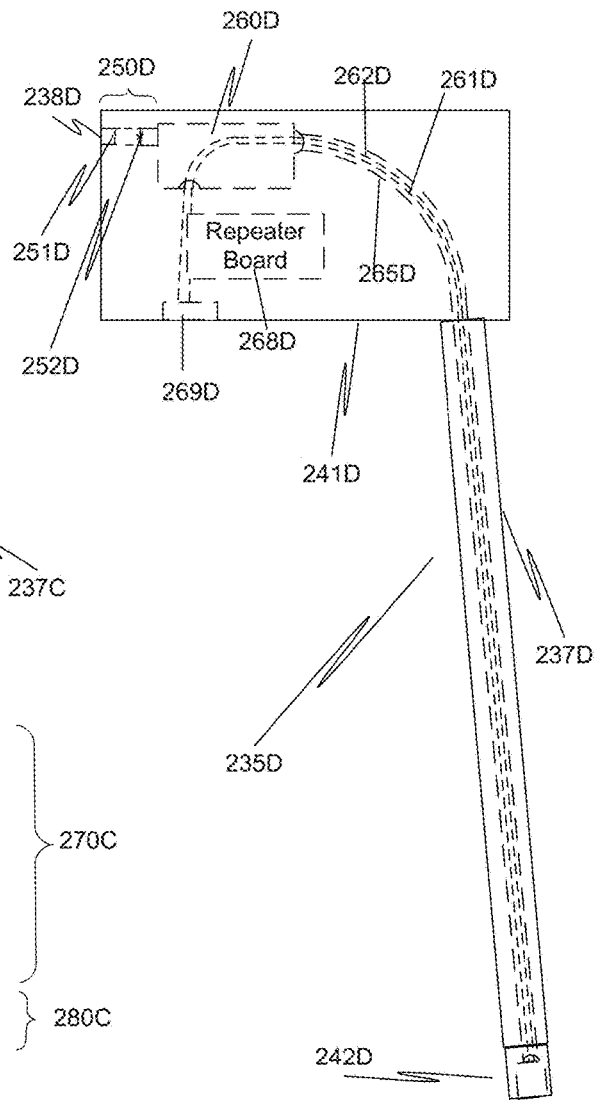
Fig. 2C Fig. 2D

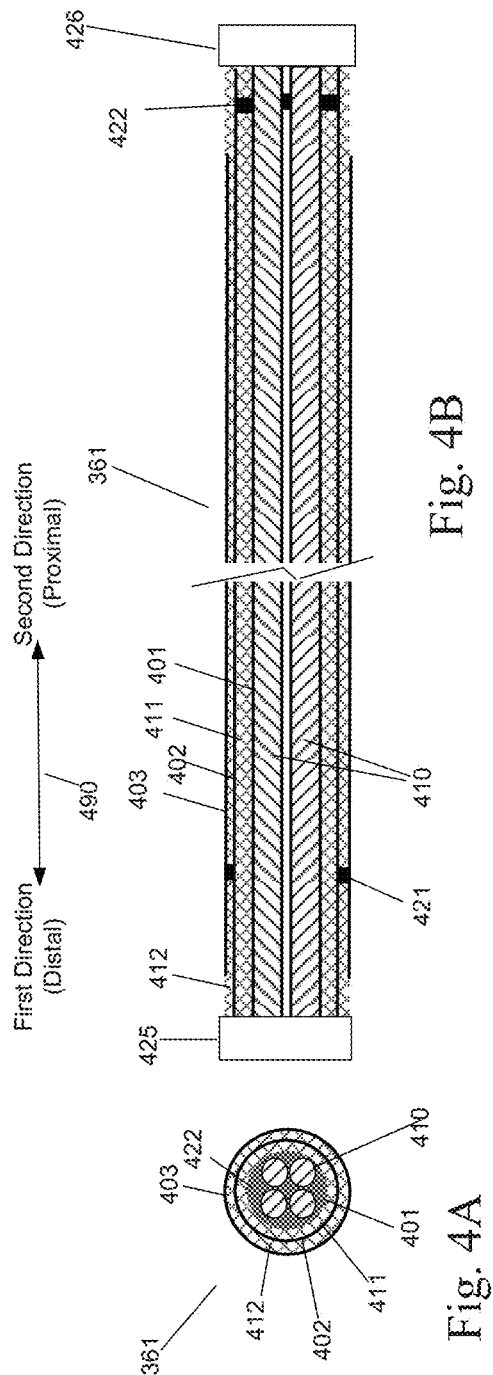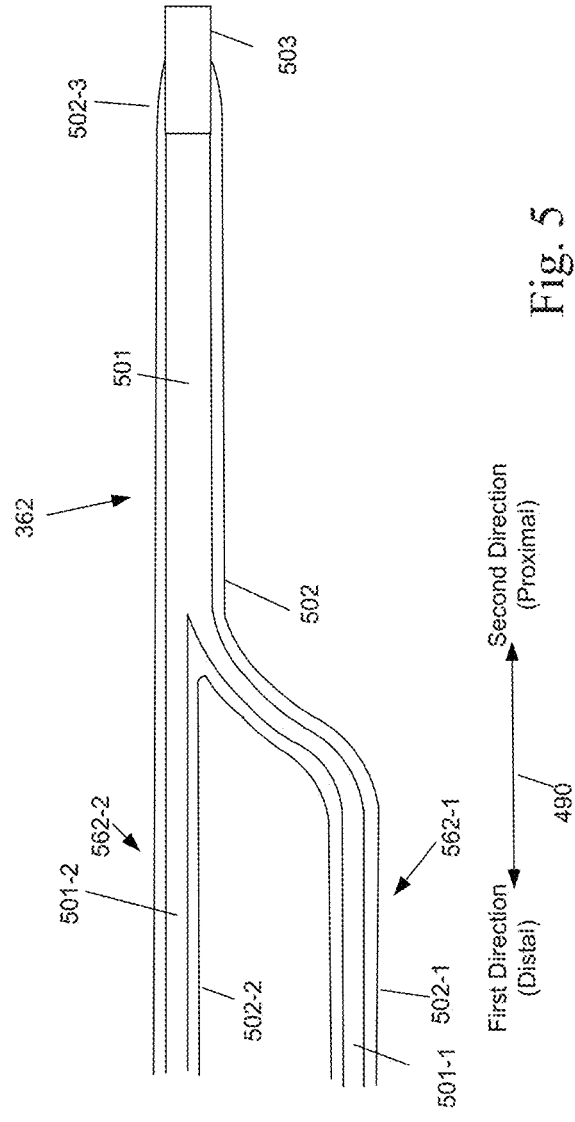

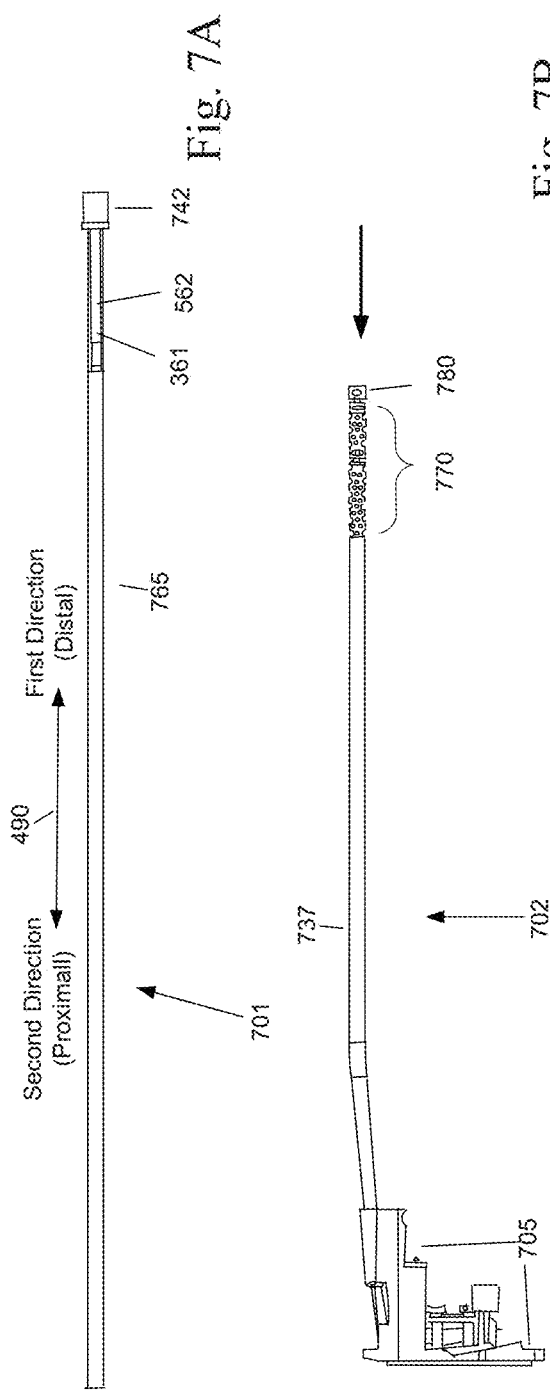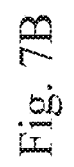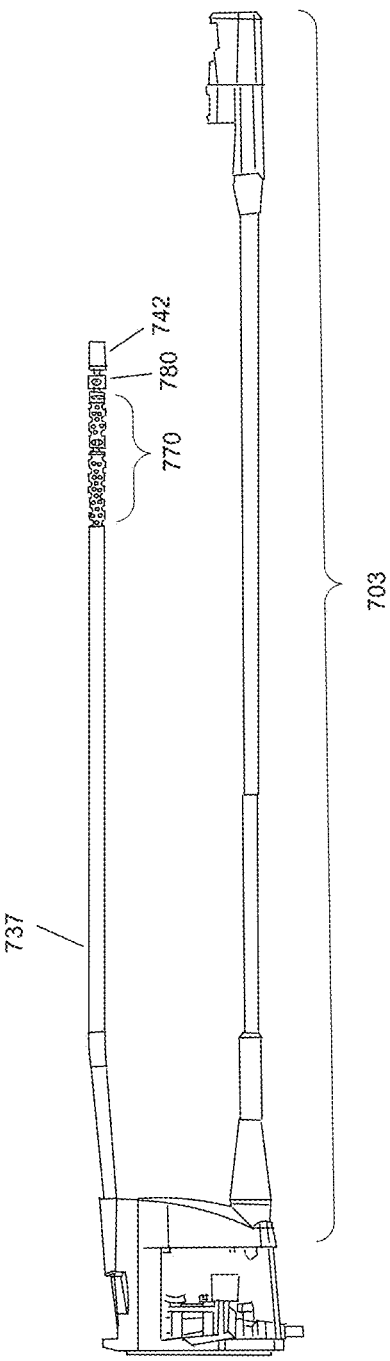

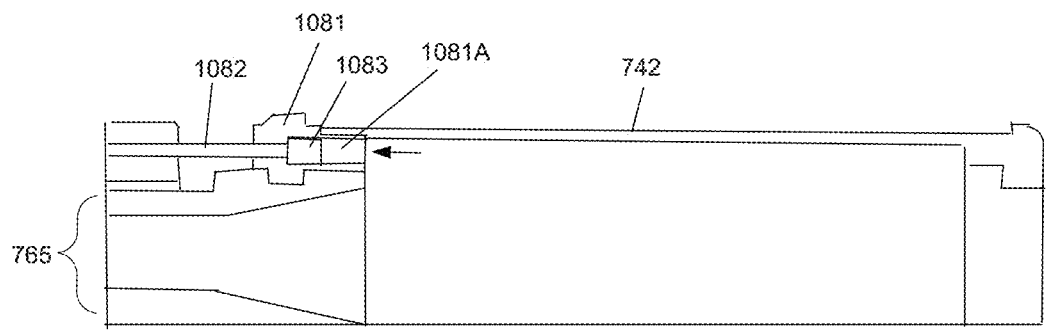
Fig. 10A
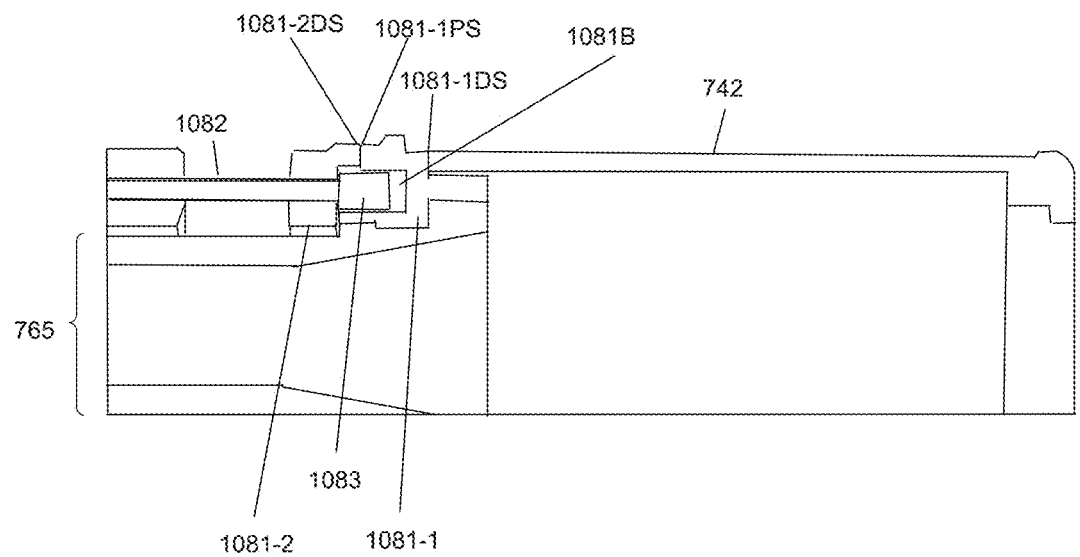
Fig. 10B
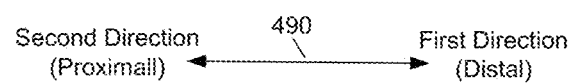

ENDOSCOPE INCLUDING A PLURALITY OF INDIVIDUALLY TESTABLE SUBASSEMBLIES

RELATED APPLICATION

This application claims priority to and the benefit of:
U.S. application Ser. No. 16/317,696 entitled "AN ENDOSCOPE INCLUDING A PLURALITY OF INDIVIDUALLY TESTABLE SUBASSEMBLIES," and filed on Jan. 14, 2019, which is a U.S. national phase of International Application No. PCT/US/2017/032082, filed May 11, 2017, which designates the U.S. and claims priority to U.S. Provisional Patent Application No. 62/362,187 entitled "AN ENDOSCOPE INCLUDING A PLURALITY OF INDIVIDUALLY TESTABLE SUBASSEMBLIES," and filed on Jul. 14, 2016, all of which are incorporated herein by reference in their entirety.

BACKGROUND OF THE INVENTION

Field of the Invention

The present invention relates generally to endoscopes, and more particularly to features that facilitate testing and assembly of an endoscope.

Description of Related Art

One or more endoscopes are commonly used in computer-assisted surgery. An endoscope usually has a shaft, either flexible or rigid, that extends into a patient's body. At the end of the endoscope in the patient's body are one or more ports that provide illumination of the surgical site and one or more ports that are used to capture an image or images of the surgical site. An electrical cable and a fiber optic cable typically extend through the shaft of the endoscope.

Since at least part of the endoscope is introduced into a patient's body during a surgical procedure, the endoscope must be cleaned and sterilized before and after each surgical procedure. Typically, the endoscope is cleaned and disinfected by scrubbing the endoscope and then placing the endoscope in a bath and subjecting the endoscope to ultrasound. The endoscope is sterilized by an autoclave process. In the autoclave process, the endoscope is subjected to a vacuum and to high pressure high temperature steam. Thus, the cleaning and sterilization processes subject the endoscope to submersion in a liquid and to a variety of pressures and temperatures. In addition, when an endoscope is shipped by air, the endoscope is also subjected to a variety of pressures and temperatures.

Finally, to assure that the endoscope is not damaged, the endoscope is pressure tested before each use. See for example, "Are You Properly Leak Testing Your Flexible Endoscope?", Fibertech Medical U.S.A., 2 pgs. (2006).

The issues associated with cleaning, sterilizing, and pressure testing are known and a variety of different approaches have been taken to address the issues. For example, U.S. Pat. No. 5,868,667 discloses a device that allows equalization of the pressure between an internal space of the endoscope and an environment outside the endoscope. This device was reported to be a vent cap that equalized the pressure while reducing the flow of any liquid, water vapor, and hydrogen peroxide into the endoscope's internal space. The vent cap was designed to receive a port connected to the internal space of the endoscope.

However, while some manufacturers make endoscopes that include a port that can accept a vent cap, the use of vent caps required using different caps depending on the process being used according to U.S. Patent Application Publication No. US 2014/0100425 A1. U.S. Patent Application Publication No. US 2014/0100425 A1 describes yet another example of a pressure compensation cap that can be placed on a port of an endoscope.

SUMMARY OF THE INVENTION

A surgical apparatus, in accordance with an embodiment, includes a housing, a pressure test chamber, and a test port retainer. The housing includes a pressure test port. The test port retainer is mounted within the housing. The test port retainer couples the pressure test port to the pressure test chamber. The test port retainer includes a test port retainer housing, a probe seal, and a liquid exclusion barrier. The probe seal and the liquid exclusion barrier are mounted within the test port retainer housing.

In one aspect, the test port retainer also includes a hydrophobic membrane mounted within the test port retainer housing. In this aspect, the liquid exclusion barrier is mounted between the probe seal and the hydrophobic membrane. In one aspect, the hydrophobic membrane is a polyvinylidene difluoride membrane, while the liquid exclusion barrier includes an X-slit valve.

The pressure test chamber includes a manifold. The test port retainer is mounted between the pressure test port and the manifold so that the pressure test port communicates with the manifold through the test port retainer.

The surgical apparatus, in accordance with an embodiment, also includes an image capture assembly. The pressure test chamber includes a central tube having a first end, a second end, and a central lumen. The central lumen extends between the first end and the second end. The first end of the central tube is affixed to the image capture assembly to form a pressure tight seal. The second end of the central tube is coupled to the test port retainer so that the pressure test port communicates with the central lumen of the central tube through the test port retainer. More specifically, the second end of the central tube is affixed to the manifold so that the pressure test port communicates with the central lumen of the central tube through the manifold.

The surgical apparatus, in accordance with an embodiment, also includes a pressure-sealed electrical cable. The pressure-sealed electrical cable is connected to the image capture assembly and extends through the central lumen into the manifold. The manifold includes a pressure seal. The pressure-sealed electrical cable extends through the pressure seal and out of the manifold.

The pressure-sealed electrical cable includes one or more conductors, a first insulating jacket surrounding the one or more conductors, a first shield surrounding the first insulating jacket, a second insulating jacket surrounding the first shield, and a first pressure seal formed around and in the first shield. In one aspect, the pressure-sealed electrical cable also includes a second shield surrounding the second insulating jacket, a third insulating jacket surrounding the second shield, and a second pressure seal is formed around and in the second shield and extending between the second insulating jacket and the third insulating jacket. The pressure-sealed electrical cable has a first end and a second end. In one aspect, the first pressure seal is adjacent one of the first end and the second end, and the second pressure seal is adjacent an other of the first end and the second end.

An endoscope, in accordance with an embodiment, includes an image capture subassembly and a central tube bundle subassembly. The image capture subassembly (a second subassembly) includes an electrical-cable and image-capture-unit subassembly (a first subassembly). The electrical-cable and image-capture-unit subassembly includes an electrical cable and an image capture unit. The electric cable is connected to the image capture unit and extends proximally from the image capture assembly. The central tube bundle subassembly (a third subassembly) includes a central tube. The central tube has a distal end. The electrical cable is passed into the distal end of the central tube in forming the central tube bundle subassembly and the electrical cable extends from the proximal end of the central tube. The distal end of the central tube is connected to the image capture subassembly. The central tube bundle subassembly also includes a light pipe coupled to the image capture assembly and extending through the central tube. In one aspect, the electrical cable is a pressure-sealed electrical cable.

In one aspect, the central tube is a single continuous tube with a single lumen. The single continuous tube has an outer surface and an inner surface. The inner surface bounds the single lumen. In a still further aspect, an antifriction coating coats both the outer surface and the inner surface of the single continuous tube.

In accordance with an embodiment, the endoscope also includes a base instrument subassembly (a fourth subassembly). The base instrument subassembly includes a base, a shaft, and optionally an articulating assembly. The shaft is coupled between the base and the articulating assembly. The central tube extends through the articulating assembly and the shaft. The articulating assembly is connected to the image capture assembly.

In one aspect, the articulating assembly includes a first disk, a second disk, an actuation cable having a distal end, and a fitting. The first and second disks upon being mated form part of an articulation joint. The distal end of the actuation cable passes through the second disk and then the fitting is attached to the distal end of the actuation cable. The fitting is contained in a cavity formed by mating the first disk to the second disk.

The base instrument subassembly, in accordance with an embodiment, also includes a manifold and a manifold pressure seal. The pressure-sealed electrical cable and the light pipe pass through the manifold pressure seal, and the manifold pressure seal is mounted in the manifold. The base instrument subassembly also includes a test port retainer mounted on the manifold.

In another aspect, an endoscope includes a pressure-sealed electrical cable connected to an image capture unit to form a first subassembly. The endoscope further includes a shell having a distal end and a proximal end. The image capture unit is mounted in the shell from the distal end of the shell with the pressure-sealed electrical cable extending proximally through the proximal end of the shell. A light pipe has a distal end of the light pipe being mounted in the shell with the light pipe extending proximally through the proximal end of the shell. A lid is affixed to the distal end of the shell. The shell, lid, the light pipe, and the first subassembly are a second subassembly.

The endoscope, in accordance with an embodiment, further includes a flange and a central tube having a distal end. The distal end of the central tube is mounted on the flange and the flange is affixed to the shell. The central tube, the flange and second subassembly are a central tube bundle subassembly.

In still yet another aspect, an endoscope, in accordance with an embodiment, includes a central tube bundle subassembly and a base instrument subassembly The central tube bundle subassembly includes an image capture assembly, a light pipe having a distal end mounted in the image capture assembly, a pressure-sealed electrical cable having a distal end connected to the image capture assembly, and a central tube having a distal end and a lumen. The distal end of central tube is connected to the image capture unit. The light pipe and the pressure-sealed electrical cable pass through the lumen of the central tube. The base instrument subassembly includes a base, a shaft, and an articulating assembly. The shaft is coupled between the base and the articulating assembly. The central tube extends through the articulating assembly and the shaft. The articulating assembly is connected to the image capture assembly.

In one aspect, the central tube of this endoscope is a single continuous tube. The single continuous tube has an outer surface and an inner surface. The inner surface bounds the single lumen. An antifriction coating coats both the outer surface and the inner surface of the single continuous tube. The pressure-sealed electrical cable has an outer surface with an antifriction coating on the outer surface of the pressure-sealed electrical cable.

In still a further aspect, an endoscope includes an image capture assembly and an articulating assembly connected to the image capture assembly. The articulating assembly includes a first disk, a second disk, an actuation cable having a distal end, and a fitting. The distal end of the actuation cable passes through the second disk and then the fitting is attached to the distal end of the actuation cable. The fitting is contained in a cavity formed by mating the first disk to the second disk. The mating of the first and second disks forms part of an articulation joint. The first disk is connected to the image capture assembly.

A method of manufacturing an endoscope, in accordance with an embodiment, includes assembling a first subassembly including a pressure-sealed electrical cable connected to an image capture unit. An electrical conductivity test is performed on the first subassembly, and then a second subassembly including the first subassembly, a shell, a light pipe, and a lid is assembled. The shell has a distal end and a proximal end. In assembling the second subassembly, the image capture unit is mounted in the shell from the distal end of the shell with the pressure-sealed electrical cable extending proximally through the proximal end of the shell. A distal end of a light pipe is mounted in the shell with the light pipe extending proximally through the proximal end of the shell. Finally, the lid is affixed to the distal end of the shell.

After the second subassembly is assembled, a seal verification test is performed on the second subassembly. Upon successful completion of the seal verification test, a central tube assembly is assembled. The central tube assembly includes the second subassembly, a central tube, and a flange. Assembling the central tube includes mounting the central tube on the flange, threading the pressure-sealed electrical cable and the light pipe through the flange and the central tube, and affixing the flange to the shell.

The central tube of the central tube assembly is threaded through a shaft of a base instrument subassembly, and then the pressure-sealed electrical cable and the light pipe are passed through a pressure seal. The pressure seal is mounted in a manifold, and the central tube is affixed to the manifold. Finally, a pressure test is performed using a port in the manifold.

Hence, in one aspect, an endoscope includes a first subassembly, a second subassembly, a third subassembly, and a fourth subassembly, which are sequentially assembled and tested in making the endoscope. The first subassembly includes a pressure-sealed electrical cable connected to an image capture unit. The second subassembly includes the first subassembly, a shell, a light pipe, and a lid. The third subassembly includes the second subassembly, a central tube, and a flange. The fourth subassembly includes the third subassembly, a base, a shaft, and optionally an articulating assembly.

BRIEF DESCRIPTION OF THE DRAWINGS

FIGS. 2A to 2D illustrate alternative aspects of the surgical apparatus of FIG. 1

FIGS. 4A and 4B are an end view and a cross-sectional view, respectively, of one aspect of a pressure-sealed electrical cable.

FIG. 5 is an illustration of a light pipe suitable for use in the surgical apparatuses of FIGS. 1, 2A to 2D, and 3.

FIG. 7A is an illustration of a central tube bundle subassembly of an endoscope.

FIG. 7B is an illustration of a base instrument subassembly of the endoscope of FIG. 7A.

FIG. 7C is an illustration of the central tube assembly of FIG. 7A installed in the base instrument subassembly of FIG. 7B and an instrument to endoscopic imaging system cable connected to the combination.

FIGS. 10A and 10B illustrate how to modify a disk of an articulating assembly to eliminate a possible fluid flow path.

Figure 1:
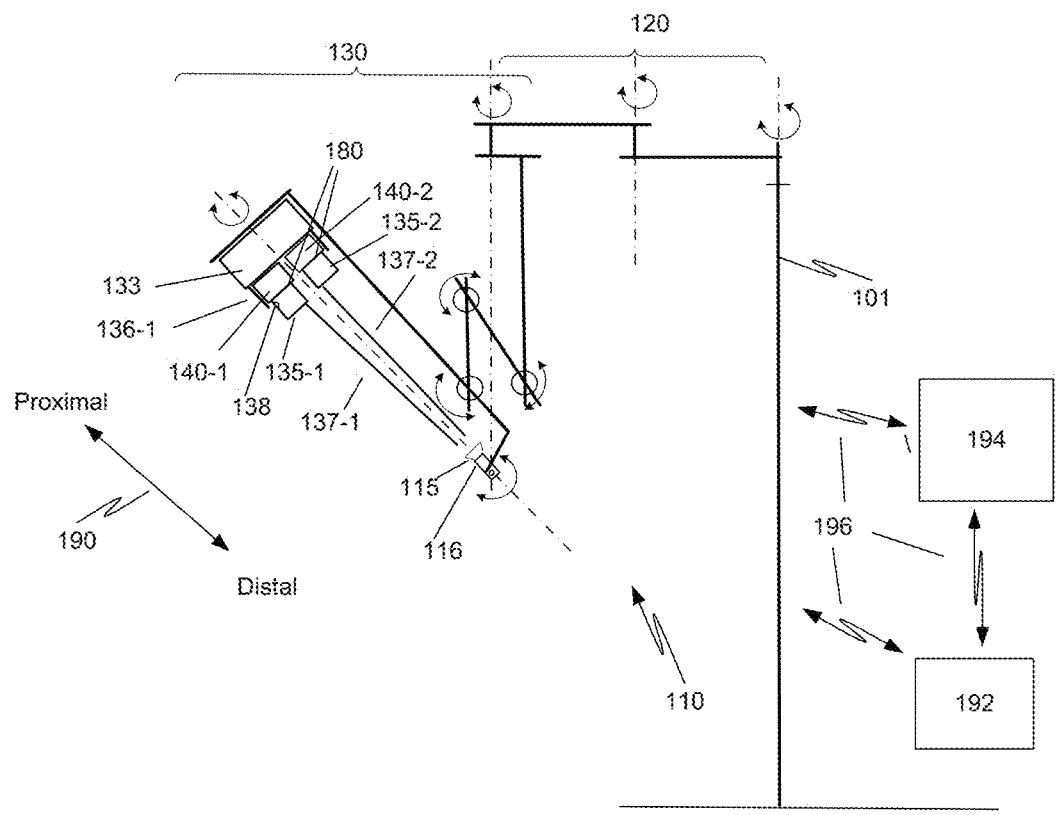
FIG. 1 is a schematic side view that illustrates aspects of a surgical system that includes a surgical apparatus with a pressure test port, a test port retainer, and a pressure test chamber.

In the drawings, for single digit figure numbers, the first digit in the reference numeral of an element is the number of the figure in which that element first appears. For double-digit figure numbers, the first two digits in the reference numeral of an element is the number of the figure in which that element first appears.

DETAILED DESCRIPTION

A novel structure and method, in accordance with an embodiment, eliminate the prior art shortcomings associated with a port of an endoscope that required some type of cap to seal that port. Even though a vent cap may provide pressure compensation and block liquids from entering the internal space of an endoscope, use of a vent cap still requires that a user remember to use and properly install the vent cap. If a user forgets to install the vent cap or improperly installs the vent cap, the endoscope can be damaged by liquid intrusion into the internal space of the endoscope during sterilization of the endoscope. As described more completely below, this problem is eliminated with a test port 138 coupled to a test port retainer that is internal to an endoscope 135-1. Endoscope 135-1 is an imaging instrument, and thus may be called instrument 135-1.

Moreover, vent caps that include a filter made from a material which passes gasses under pressure, but prevents liquids from passing through may give false positives during pressure testing. If the filter is covered with a liquid or is wet during a pressure test, gas is blocked from passing through the filter, and so the pressure tester sees a positive pressure. However, this positive pressure is not the result of internal space of the endoscope being properly sealed, but rather is the result of the membrane not being able to pass the gas due to the moisture on or covering the filter. Also, as described more completely below, not only is the reliance on a vent cap eliminated, but also, the test port retainer coupled to test port 138 assures that no moisture or liquid blocks flow of a gas into the internal space of endoscope 135-1 during pressure testing of endoscope 135-1.

FIG. 1 is a schematic side view that illustrates aspects of a computer-assisted teleoperated surgical system 100 that includes an endoscopic imaging system 192, a surgeon's console 194 (master), and a patient side support system 110 (slave), all interconnected by wired (electrical or optical) or wireless connections 196. One or more electronic data processors may be variously located in these main components to provide system functionality. Examples are disclosed in U.S. Pat. No. 9,060,678 B2, which is incorporated by reference herein.

Patient side support system 110 includes an entry guide manipulator 130. At least one surgical device assembly is coupled to the entry guide manipulator. Each surgical device assembly includes an instrument that in turn includes either a surgical instrument or an image capture assembly. For example, in FIG. 1, one surgical device assembly includes an instrument 135-1 with a shaft 137-1 and an image capture assembly that extends through entry guide 115 during a surgical procedure. Instrument 135-1 is sometimes referred to an endoscope, or alternatively as an imaging system device or camera instrument. Instrument 135-1 includes a novel test port retainer that connects test port 138 to a manifold in a pressure test chamber, as described more completely below, within instrument 135-1. Typically, entry guide 115 includes a plurality of lumens.

Imaging system 192 performs image processing functions on, e.g., captured endoscopic imaging data of the surgical site and/or preoperative or real time image data from other imaging systems external to the patient. Imaging system 192 outputs processed image data (e.g., images of the surgical site, as well as relevant control and patient information) to a surgeon at surgeon's console 194. In some aspects, the processed image data is output to an optional external monitor visible to other operating room personnel or to one or more locations remote from the operating room (e.g., a surgeon at another location may monitor the video; live feed video may be used for training; etc.).

Surgeon's console 194 includes multiple degrees-of-freedom ("DOF") mechanical input devices ("masters") that allow the surgeon to manipulate the instruments, entry guide(s), and imaging system devices, which are collectively referred to as slaves. These input devices may in some aspects provide haptic feedback from the surgical device assembly components to the surgeon. Console 194 also includes a stereoscopic video output display positioned such that images on the display are generally focused at a distance that corresponds to the surgeon's hands working behind/below the display screen. These aspects are discussed more fully in U.S. Pat. No. 6,671,581, which is incorporated by reference herein.

Control during insertion of the instruments may be accomplished, for example, by the surgeon moving the instruments and/or image capture assembly presented in the image with one or both of the masters; the surgeon uses the masters to move the instrument in the image side to side and to pull the instrument towards the surgeon. The motion of the masters commands the imaging system and an associated surgical device assembly to steer towards a fixed center point on the output display and to advance inside the patient.

In one aspect, the camera control is designed to give the impression that the masters are fixed to the image so that the image moves in the same direction that the master handles are moved. This design causes the masters to be in the correct location to control the instruments when the surgeon exits from camera control, and consequently this design avoids the need to clutch (disengage), move, and declutch (engage) the masters back into position prior to beginning or resuming instrument control.

In some aspects the master position may be made proportional to the insertion velocity to avoid using a large master workspace. Alternatively, the surgeon may clutch and declutch the masters to use a ratcheting action for insertion. In some aspects, insertion may be controlled manually (e.g., by hand operated wheels), and automated insertion (e.g., servomotor driven rollers) is then done when the distal end of the surgical device assembly is near the surgical site. Preoperative or real time image data (e.g., MRI, X-ray) of the patient's anatomical structures and spaces available for insertion trajectories may be used to assist insertion.

Patient side support system 110 includes a floor-mounted base 101, or alternately a ceiling mounted base (not shown). Base 101 may be movable or fixed (e.g., to the floor, ceiling, wall, or other equipment such as an operating table).

Base 101 supports an arm assembly that includes a passive, uncontrolled setup arm assembly 120 and an actively controlled manipulator arm assembly 130. The actively controlled manipulator arm assembly 130 is referred to as entry guide manipulator 130.

Cannula 116 is removably coupled to a cannula mount. In this description, a cannula is typically used to prevent an instrument or an entry guide from rubbing on patient tissue. Cannulas may be used for both incisions and natural orifices. For situations in which an instrument or an entry guide does not frequently translate or rotate relative to its insertion (longitudinal) axis, a cannula may not be used. For situations that require insufflation, the cannula may include a seal to prevent excess insufflation gas leakage past the instrument or entry guide. Examples of cannula assemblies which support insufflation and procedures requiring insufflation gas at the surgical site may be found in U.S. patent application Ser. No. 12/705,439 (filed Feb. 1, 2010; disclosing "Entry Guide for Multiple Instruments in a Single Port System"), the full disclosure of which is incorporated by reference herein for all purposes. For thoracic surgery that does not require insufflation, the cannula seal may be omitted, and if instruments or entry guide insertion axis movement is minimal, the cannula itself may be omitted. A rigid entry guide may function as a cannula in some configurations for instruments that are inserted relative to the entry guide. Cannulas and entry guides may be, e.g., steel or extruded plastic. Plastic, which is less expensive than steel, may be suitable for one-time use.

The various passive setup joints/links and active joints/links allow positioning of instrument manipulators to move the instruments with a large range of motion when a patient is placed in various positions on a movable table. In some embodiments, a cannula mount may be coupled to the first manipulator link.

Certain setup and active joints and links in the manipulator arm may be omitted to reduce the surgical system's size and shape, or joints and links may be added to increase degrees of freedom. It should be understood that the manipulator arm may include various combinations of links, passive joints, and active joints (redundant DOFs may be provided) to achieve a necessary range of poses for surgery. Furthermore, various instruments alone or surgical device assemblies including entry guides, multiple instruments, and/or multiple entry guides, and instruments coupled to instrument manipulators (e.g., actuator assemblies) via various configurations (e.g., on a proximal face or a distal face of the instrument transmission means or the instrument manipulator), are applicable in aspects of the present disclosure.

Each of plurality of surgical device assemblies 180 includes an instrument manipulator assembly and an instrument including one of a surgical instrument and an image capture assembly. In FIG. 1, two of a plurality of surgical device assemblies 180 are visible, and each of the two visible surgical device assemblies includes an instrument manipulator assembly while one has a surgical instrument and the other an image capture assembly. Each of instrument manipulator assemblies 140-1 and 140-2 is computer-assisted, in one aspect, and so each is sometimes referred to as a computer-assisted instrument manipulator assembly. Each of instrument manipulator assemblies 140-1, 140-2 is coupled to entry guide manipulator assembly 133 by a different insertion assembly, e.g. instrument manipulator assembly 140-1 is coupled to entry guide manipulator assembly 133 by insertion assembly 136-1.

In one aspect, insertion assembly 136-1 is a telescoping assembly that moves the corresponding surgical device assembly away from and towards entry guide manipulator assembly 133. In FIG. 1, insertion assembly 136-1 is in a fully retracted position.

Each instrument manipulator assembly 140-1, 140-2 includes a plurality of motors that drive a plurality of outputs in an output interface of instrument manipulator assembly 140-1, 140-2. Each of instruments 135-1, 135-2 includes a body that houses a transmission unit. The transmission unit includes an input interface including a plurality of inputs. Each of instruments 135-1, 135-2 also includes a shaft 137-1, 137-2 sometimes referred to as a main tube that extends in the distal direction from the body. An end effector is coupled to a distal end of the shaft of one instrument assembly, and an image capture assembly, e.g., a camera, is included in a distal end of a different instrument assembly. See U.S. Patent Application Publication No. 2016/0184037, which is incorporated by reference, for one example of an instrument manipulator assembly and a surgical instrument.

Each of instruments 135-1, 135-2 is coupled to the instrument mount interface of a corresponding instrument manipulator assembly 140-1, 140-2 so that a plurality of inputs in an input interface of the transmission unit in instrument 135-1, 135-2 are driven by plurality of outputs in the instrument mount interface of instrument manipulator assembly 140-1, 140-2. See U.S. Patent Application Publication No. 2016/0184037.

In one aspect, one or more instrument manipulator assemblies may be configured to support and actuate a particular type of instrument, such as instrument 135-1. As shown in FIG. 1, the shafts of plurality of surgical device assemblies 180 extend distally from bodies of the instruments. The shafts extend through a common cannula 116 placed at the entry port into the patient (e.g., through the body wall or at a natural orifice). In one aspect, an entry guide 115 is positioned within cannula 116, and each instrument shaft extends through a channel in entry guide 115, so as to provide additional support for the instrument shafts.

The surgeries that can be performed using surgical system 100 may be performed on different regions of the body. For example, one surgery may be performed through the mouth of a patient. Another surgery may be performed between the ribs of the patient. Other surgeries may be performed through other orifices of the patient or through an incision in the patient. Each different entry into a patient may require a different shape and/or different size of an entry guide. Thus, an appropriate entry guide 115 is selected for a particular surgery.

FIGS. 2A to 2D are different aspects of endoscope 135-1. In FIGS. 2A to 2D, only the aspects of endoscope 135-1 needed to understand the inventive aspects are illustrated. Some of these aspects are shown with dashed lines to indicate that the aspects are included within the endoscope.

Endoscope 235A (FIG. 2A) includes a housing 241A from which a hollow shaft 237A extends. In this aspect, connected in series to a distal end of shaft 237A are a parallel motion mechanism 270A and a wrist joint assembly 280A, which are examples of articulating assemblies. An image capture assembly 242A is connected to parallel motion mechanism 270A by wrist joint assembly 280A.

A test port retainer 250A connects pressure test port 238A in housing 241A to a pressure test chamber. The pressure test chamber includes test port retainer 250A, a manifold 260A, and a central tube 265A.

Test port retainer 250A connects pressure test port 238A to manifold 260A. When endoscope 235A is not being pressure tested, test port retainer 250A allows any pressurized gases in the pressure test chamber to be vented. Thus, there is not a possibility of pressure build-up in the interior of endoscope 235A during the autoclave process which heats endoscope 235A to around 140° C. or during transport of endoscope 235A. When endoscope 235A is being cleaned, either manually or in an ultrasound bath, test port retainer 250A prevents any liquid or any moisture from passing through test port retainer 250A into the interior of the pressure test chamber.

Manifold 260A is connected between test port retainer 250A and central tube 265A. A first end of central tube 265A is connected to image capture assembly 242A by a pressure tight seal and a second end of central tube 265A is connected to manifold 260A by another pressure tight seal. Herein, a pressure tight seal means a seal that is sufficient to maintain a minimum pressure required during a pressure test.

Figures 2A, 2B:
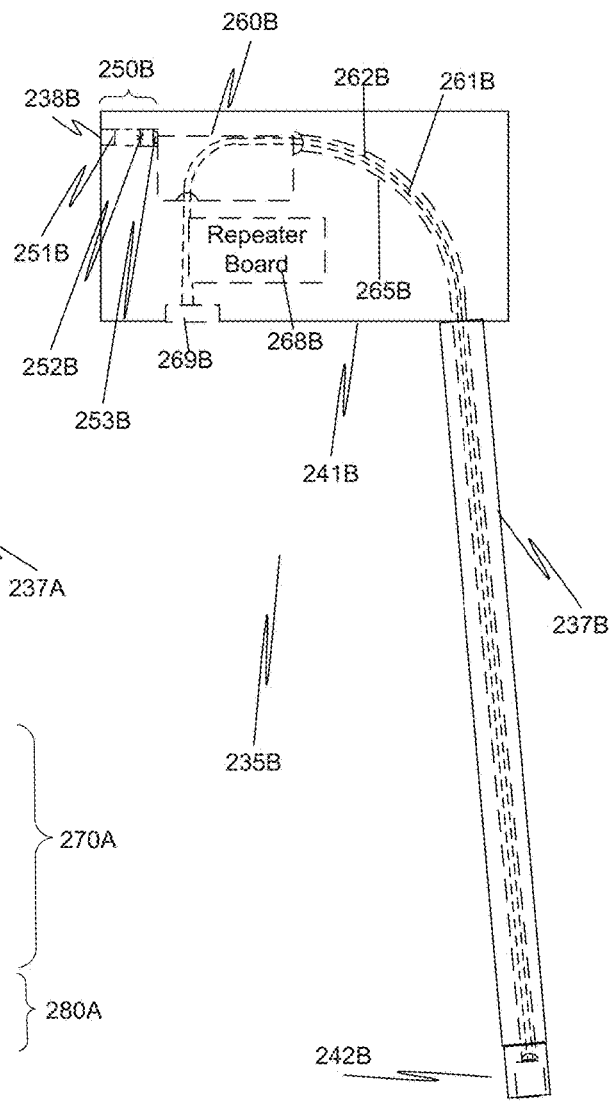

Thus, in this aspect, central tube 265A is a single continuous tube with a single lumen or channel, and in another aspect is a molded single continuous silicone tube with a single lumen. Central tube 256A has an outer surface and an inner surface. The inner surface bounds the single lumen. As illustrated in FIG. 2A, a lengthwise axis of central tube 265 is coincident with a lengthwise axis of shaft 237A, a lengthwise axis of parallel motion mechanism 270A, and a lengthwise axis of wrist joint assembly 280A as central tube 265 passes through parallel motion mechanism 270A and wrist joint assembly 280A.

Typically, image capture assembly 242A includes one or more cameras and one or more illumination ports. A pressure-sealed electrical cable 261A, sometimes referred to as cable 261A, is connected to the one or more cameras and extends through the central lumen of central tube 265A and through a first opening in manifold 260A into an interior volume of manifold 260A and out of manifold 260A. Specifically, pressure-sealed electrical cable 261A has a distal end connected to image capture assembly 242A. Pressure-sealed electrical cable 261A passes through the single lumen in central tube 365A, through and out of manifold 260A, and a proximal end of pressure-sealed electrical cable 261A is connected to repeater board 268A.

Pressure-sealed electrical cable 261A, in one aspect, is a shielded cable with one or more conductors. Each of the one or more of conductors is connected to a connector that in turn is connected to the one or more cameras. The one or more conductors are potted in the connector. The shield or shields of cable 261 are also pressure-sealed. Herein, pressure-sealed means that a seal is formed in and around the shield that is sufficient to maintain the minimum pressure required during a pressure test. Thus, a pressure-sealed electrical cable is a cable that does not have a through path for gas flow between insulating jackets or a through path for gas flow within a part of the electrical cable, such as the shield, which would prevent the endoscope from maintaining the minimum pressure required during a pressure test.

In this aspect, light emitting diodes on repeater board 268A are used to indicate whether a laser on. Thus, endoscope 235A includes at least one light pipe 262A that has a first end connected to an illumination port in image capture assembly 242A and a second end potted in a metal ferrule that is connected to connector 269A. Both ends of light pipe 262A are mounted so that the connections are pressure-sealed. Light pipe 262A extends through the central lumen of central tube 265A also.

Use of light pipe 262A is illustrative only and is not intended to be limiting. If the illuminator is included in image capture assembly 242A, light pipe 262A would not be used.

Cable 261A and light pipe 262A enter manifold 260A through a first opening and exit through a second opening. In one aspect, a pressure seal is used around cable 261A and light pipe 262A in the first and second openings. In another aspect, manifold 260A is configured so that a single pressure seal is used.

Repeater board 268A is connected to connector 269A. An instrument to endoscopic imaging system cable is connected to connector 269A to couple endoscope 235A to an endoscopic image system, such as endoscopic imaging system 192.

Test port retainer 250A includes a body, a probe seal 251A, a liquid exclusion barrier 252A, and a hydrophobic membrane 253A. Each of probe seal 251A, liquid exclusion barrier 252A, and hydrophobic membrane 253A are mounted within the body of test port retainer 250A with probe seal 251A being closest to pressure test port 238A and hydrophobic membrane 253A being farthest from pressure test port 238A, i.e., liquid exclusion barrier 252A is mounted between probe seal 251A and hydrophobic membrane 253A.

Probe seal 251A has an opening in the center that is designed to form a seal around a tip of a pressure test probe. Liquid exclusion barrier 252A is an x-slit valve, in one aspect. If there is a pressure differential across the x-slit valve, the x-slit valve opens until the pressure equalizes. When endoscope 235A is cleaned, the water pressure on x-slit valve is not sufficient to cause x-slit valve to open, and so x-slit valve prevents liquid from entering the pressure test chamber including the manifold and the central lumen of the central tube.

In one aspect, hydrophobic membrane 253A is a polyvinylidene difluoride (PVDF) membrane with 0.22 to 0.45 micrometer pore sizes. PVDF is resistant to solvents and is a highly non-reactive and pure thermoplastic fluoropolymer produced by the polymerization of vinylidene difluoride. PVDF melts at around 177 C, which is higher than the temperatures encountered during the autoclave process. Hydrophobic membrane 253A protects the pressure test chamber from ultra-sound fluids and prevents any pressure build up inside the pressure test chamber during the autoclave process.

In addition, liquid exclusion barrier 252A keeps moisture and liquids away hydrophobic membrane 253A so that membrane 253A operates properly during a pressure test. In prior art systems, if a hydrophobic membrane were wet, the hydrophobic membrane could result in a false positive pressure reading because the moisture prevented the gas used in the pressure test from passing through the hydrophobic membrane. Test port retainer 250A eliminates the likelihood of such false positive pressure readings by preventing moisture and/or a liquid from reaching the surface of hydrophobic membrane 253A.

To assure that there are no leaks from the environment outside endoscope 235A into the pressure test chamber, a pressure test probe is inserted into test port 238A and the pressure test chamber is pressurized to a predetermined pressure. If the pressure test chamber holds the pressure to greater than a predetermined minimum pressure for a predetermined time interval, there are no fluid (liquid or gas) pathways for communication between the environment outside endoscope and the interior of pressure test chamber that are of significance during a surgical procedure. Consequently, pressure test chamber cannot be contaminated during a surgical procedure in which endoscope 235A is used at insufflation pressure.

In another aspect, endoscope 235B (FIG. 2B) includes a housing 241B from which a shaft 237B extends. In this aspect, an image capture assembly 242B is connected to a distal end of shaft 237A.

A test port retainer 250B connects pressure test port 238B in housing 241B to a pressure test chamber. The pressure test chamber includes test port retainer 250B, a manifold 260B, and a central tube 265B. Manifold 260B is connected between test port retainer 250B and central tube 265B.

The configuration and construction of repeater board 268B, connector 269B, test port retainer 250B including a probe seal 251B, a liquid exclusion barrier 252B, and a hydrophobic membrane 253B, manifold 260B, and central tube 265B including a pressure-sealed electrical cable 261B and a light pipe 262B are the same as repeater board 268A, connector 269A, test port retainer 250A including a probe seal 251A, a liquid exclusion barrier 252A, and a hydrophobic membrane 253A, manifold 260A, and central tube 265A including pressure-sealed electrical cable 261A and light pipe 262A, respectively. Therefore, the description of test port retainer 250A including a probe seal 251A, a liquid exclusion barrier 252A, and a hydrophobic membrane 253A, manifold 260A, and central tube 265A including cable 261A and light pipe 262A is not repeated here.

In another aspect, endoscope 235C (FIG. 2C) includes a housing 241C to which a shaft 237C extends. In this aspect, connected in series to a distal end of shaft 237C are a parallel motion mechanism 270C and a wrist joint assembly 280C. An image capture assembly 242C is connected to the parallel motion mechanism 270C by wrist joint assembly 280C.

A test port retainer 250C connects pressure test port 238C in housing 241C to a pressure test chamber. The pressure test chamber includes a test port retainer 250C, a manifold 260C, and a central tube 265C. Manifold 260C is connected between test port retainer 250C and central tube 265C.

The configuration and construction of repeater board 268C, connector 269C, parallel motion mechanism 270C, wrist joint assembly 280C, manifold 260C, and central tube 265C including pressure-sealed electrical cable 261C and light pipe 262C, and image capture assembly 242C are the same as repeater board 268A, connector 269A, parallel motion mechanism 270A, wrist joint assembly 280A, manifold 260A, and central tube 265A including pressure-sealed electrical cable 261A and light pipe 262A, and image capture assembly 242A, respectively. Therefore, the description of parallel motion mechanism 270A, wrist joint assembly 280A, manifold 260A, and central tube 265A including cable 261A and light pipe 262A, and image capture assembly 242A are not repeated here.

Test port retainer 250C includes a body, a probe seal 251C, and a liquid exclusion barrier 252C. Probe seal 251C and liquid exclusion barrier 252C are mounted within the body of test port retainer 250C with probe seal 251C being closest to pressure test port 238C and liquid exclusion barrier 252C being farthest from pressure test port 238C.

In another aspect, endoscope 235D (FIG. 2D) includes a housing 241D from which a shaft 237D extends. In this aspect, an image capture assembly 242D is connected to a distal end of shaft 237D.

A test port retainer 250D connects pressure test port 238D in housing 241D to a pressure test chamber. The pressure test chamber includes a test port retainer 250D, a manifold 260D, and a central tube 265D. Manifold 260D is connected between test port retainer 250D and central tube 265B.

The configuration and construction of repeater board 268D, connector 269D, test port retainer 250D including probe seal 251D and liquid exclusion barrier 252D, manifold 260D, central tube 265D including cable 261D and light pipe 262D, and image capture assembly 242D are the same as repeater board 268C, connector 269C, test port retainer 250C including a probe seal 251C and liquid exclusion barrier 252C, manifold 260C, central tube 265C including cable 261C and light pipe 262C, and image capture assembly 242C, respectfully. Therefore, the description of test port retainer 250C including a probe seal 251C and liquid exclusion barrier 252C, manifold 260C, central tube 265C including cable 261C and light pipe 262C, and image capture assembly 242C are not repeated here.

Figure 3:
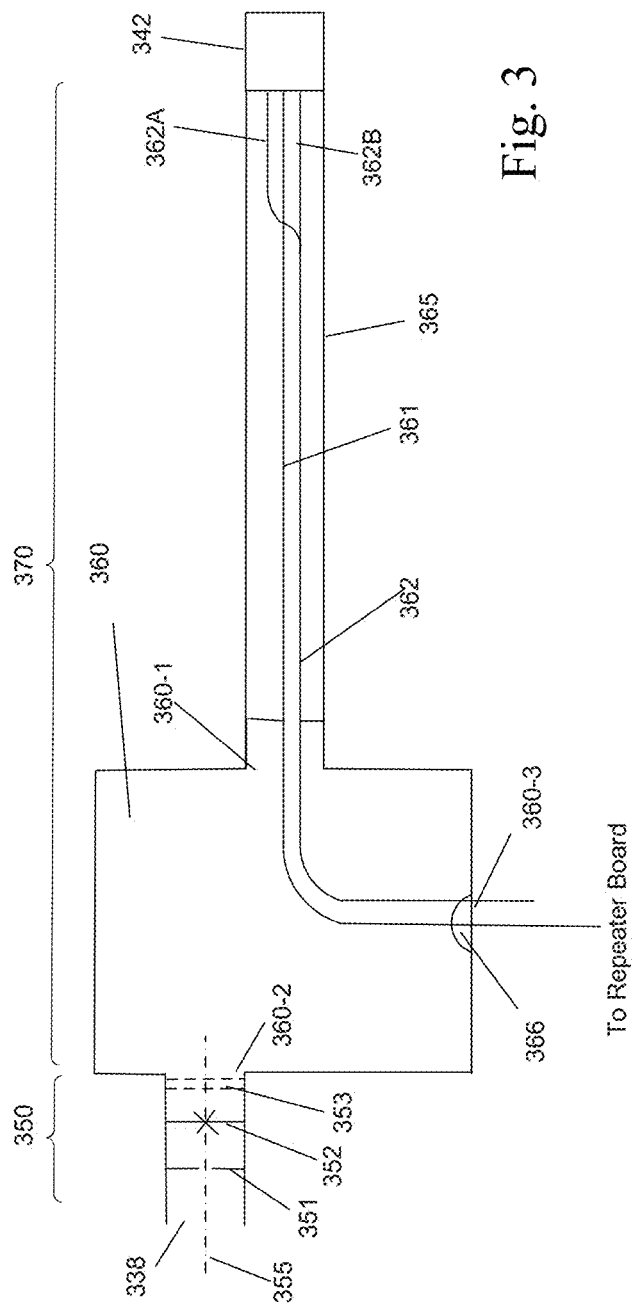
FIG. 3 is a more detailed schematic illustration of a test port retainer and a pressure test chamber, which are suitable for use in any of the surgical apparatuses of FIGS. 1 and 2A to 2D.

FIG. 3 is a more detailed schematic illustration of test port retainer 350 and pressure test chamber 370, which are suitable for use in any one of endoscopes 235A to 235D. Pressure test port 338 in the housing of the endoscope is a first opening in test port retainer 350. Test port retainer 350 includes a probe seal 351 and a liquid exclusion barrier 352, and optionally a hydrophobic membrane 353. Pressure test chamber 370, in this aspect, includes a manifold 360 and a central tube 365.

Test port retainer 350 includes a first opening, which is pressure test port 338, into an interior volume of test port retainer 350. A second opening into the interior volume of test port retainer 350 communicates with a second opening 360-2 in manifold 360, i.e., at least a portion of the second opening of test port retainer 350 is coincident with second opening 360-2 of manifold 360.

Probe seal 351 is mounted in the interior volume of test port retainer 350 closest to pressure test port 338 (as measured along a lengthwise axis 355 of test port retainer 350 from a center of probe seal 351 to a center of pressure test port 338) and most distance from second opening 360-2 in manifold 360. Optional hydrophobic membrane 353 is mounted in the interior volume of test port retainer 350 closest to second opening 360-2 in manifold 360 (as measured along lengthwise axis 355 of test port retainer 350 from a center of hydrophobic membrane 353 to a center of second opening 360-2 in manifold 360) and most distance from pressure test port 338.

When optional hydrophobic membrane 353 is included in test port retainer 350, liquid exclusion barrier 352 is mounted in the interior volume of test port retainer 350 between probe seal 351 and optional hydrophobic membrane 353. The centers of each of probe seal 351 and liquid exclusion barrier 352 and hydrophobic membrane 353 are intersected by lengthwise axis 355 of test port retainer 350, in this aspect. When optional hydrophobic membrane 353 is not included in test port retainer 350, liquid exclusion barrier 352 is mounted in the interior volume of test port retainer 350 closest to second opening 360-2 in manifold 360 (as measured along lengthwise axis 355 of test port retainer 350 from a center of liquid exclusion barrier 352 to a center of second opening 360-2 in manifold 360) and most distance from pressure test port 338.

Similar to the probe seals described above, probe seal 351 has an opening in its center that has a shape that forms a pressure seal around a tip of a pressure test probe when the tip is inserted through probe seal 351. In one aspect, the shape of the opening is selected to be the same as the cross-sectional shape of outside surface of the tip of the pressure test probe that is inserted into test port 338.

Similar to the liquid exclusive barriers described above, liquid exclusion barrier 352 is an x-slit valve, in one aspect. Also, as described above for the hydrophobic membranes, in one aspect, hydrophobic membrane 353 is a PVDF membrane.

In this aspect, manifold 360 includes three openings 360-1, 360-2, and 360-3. First opening 360-1 is in a flange and communicates with a central lumen of central tube 365. A piece of heat shrink tubing is fit over a second end of central tube 365 and the second end of central tube 365 is forced onto the flange. Next, the heat shrink tubing is moved over the second end of central tube and the flange and shrunk. The combination of the pressure fit of the central tube to the manifold flange and the force supplied by the heat shrink is sufficient to provide a pressure tight seal. A first end of central tube 356 is forced on a flange that is welded to camera module 342, sometimes referred to as image capture assembly 342.

A pressure-sealed electrical cable 361, sometimes referred to as cable 361, and two light pipes 362A and 362B extend in a proximal direction from a proximal end of image capture assembly 342. The two light pipes 362A and 262B merge into a single light pipe 362 that passes through the central lumen of central tube 365 through first opening 360-1 into the inner volume of manifold 360. The use of two light pipes is illustrative only, i.e., optional, and is not intended to be limiting. In other aspects, a single light pipe or no light pipes could be used.

Cable 361 and light pipe 362 exit the inner volume of manifold 360 through third opening 360-3. A pressure seal 366 surrounds cable 361 and light pipe 362 in third opening 360-3. In one aspect, pressure seal 366 is made from a two-part, platinum-catalyzed, heat-cured silicone elastomer. A two-part, platinum-catalyzed, heat-cured silicone elastomer suitable for use in making pressure seal 366 is sold by Dow Corning® under the tradename QP1-20 Liquid Silicone Rubber.

FIGS. 4A and 4B are an end view and a cross-sectional view, respectively, of one aspect of pressure-sealed electrical cable 361. Arrow 490 defines first and second directions. In one aspect, the first direction is a distal direction and the second direction is a proximal direction.

In this aspect, cable 361 is a double shielded cable. Each of a plurality of conductors 410 of cable 361 is surrounded by its own insulating jacket 401. A first braided shield 411 surrounds plurality of conductors 410. A second insulating jacket 402 surrounds first braided shield 411. A second braided shield 412 surrounds second insulating jacket 402, and a third insulating jacket 403 surrounds second braided shield 412. In one aspect, third insulating jacket 403 does not extend the full length of cable 361. In one aspect, third insulating jacket 403 is a silicone insulating jacket. The ends of third insulating jacket 402 are removed from the ends of cable 361 to facilitate connecting cable 361 to connectors 426, 425. In cable 361, the insulating jackets are electrically insulating jackets.

Prior to connecting connectors 425 and 426 to the two ends of cable 361, a strip of outer insulating jacket 403 is removed near a first end of cable 361 to expose the outer circumferential surface of second braided shield 412. (In FIG. 4B, first end of cable 361 is adjacent connector 425, which is an image capture unit connector.) A piece of heat shrink tubing is affixed to third insulating jacket 403 adjacent an edge of the exposed braided shield. Silicone is injected into the heat shrink tube around the exposed outer circumferential surface of second braided shield 412 and then the heat shrink tube is shrunk to replace the removed strip of third insulating jacket 403. The shrinking of the heat shrink tube forces the silicone into any openings in second braided shield 412 to form a first pressure seal 421 in and around second braided shield 412.

After pressure seal 421 is formed, connector 425 is affixed to the second end of cable 361. A first end of each of plurality of conductors 410 is potted in connector 425.

To form a pressure seal in first braided shield 411 and around plurality of conductor 410, second braided shield 412 is pushed back from a second end of cable 361 that connects to connector 426. A strip of second insulating jacket 402 is removed to expose the outer circumference of first braided shield 411. A piece of heat shrink tubing is affixed to second insulating jacket 402 adjacent an edge of the exposed first braided shield 411. Silicone is injected into the heat shrink tube around the exposed outer circumference of first braided shield 441 and around plurality of conductors 410. Next, the heat shrink tube is shrunk to replace the removed strip of second insulating jacket 402. The shrinking of the heat shrink tube forces the silicone into any openings in first braided shield and around openings between plurality of conductors 410 and the silicone is injected around and between plurality of conductors 410. Plurality of conductors 410 may comprise a plurality of wires. This forms a second pressure seal 422 in and around first braided shield 411 and around plurality of conductors 410. After pressure seal 422 is formed second braided shield 412 is returned to its proper position and connector 426 is affixed to the second end of cable 361. Each of plurality of conductors 410 is potted in connector 426.

In another aspect, seals 421 and 422 are made during the process of manufacturing the cable. Also, in one aspect, the outer surface of all the insulating jackets is coated with an anti-friction coating during the manufacturing of the cable.

FIG. 5 is an example of a light pipe 362 suitable for use in the surgical apparatuses of FIGS. 1, 2A to 2D, and 3. Light pipe 362 includes a fiber optic bundle 501, a protective sheath 502, and a ferrule 503. A first end, a distal end, of fiber optic bundle 501 is split into two smaller fiber optic bundles 501-1 and 501-2. A second end of fiber optic bundle 501 is potted in ferrule 503

Protective sheath 502 has a first end 502-1 and a second end 502-2 that are both open in FIG. 5, and a third end 502-3 that is sealed to the outer circumferential surface of ferrule 503. When fiber optic bundle 501 is connected to image capture assembly 342, first end 502-1 and second end 502-2 of protective sheath 502 are sealed within image capture assembly 342 so that there is not a fluid flow pathway between the outer surface of fiber optic bundle 501 and the inner surface of protective sheath 502 that is of significance during a surgical procedure.

Figure 6:
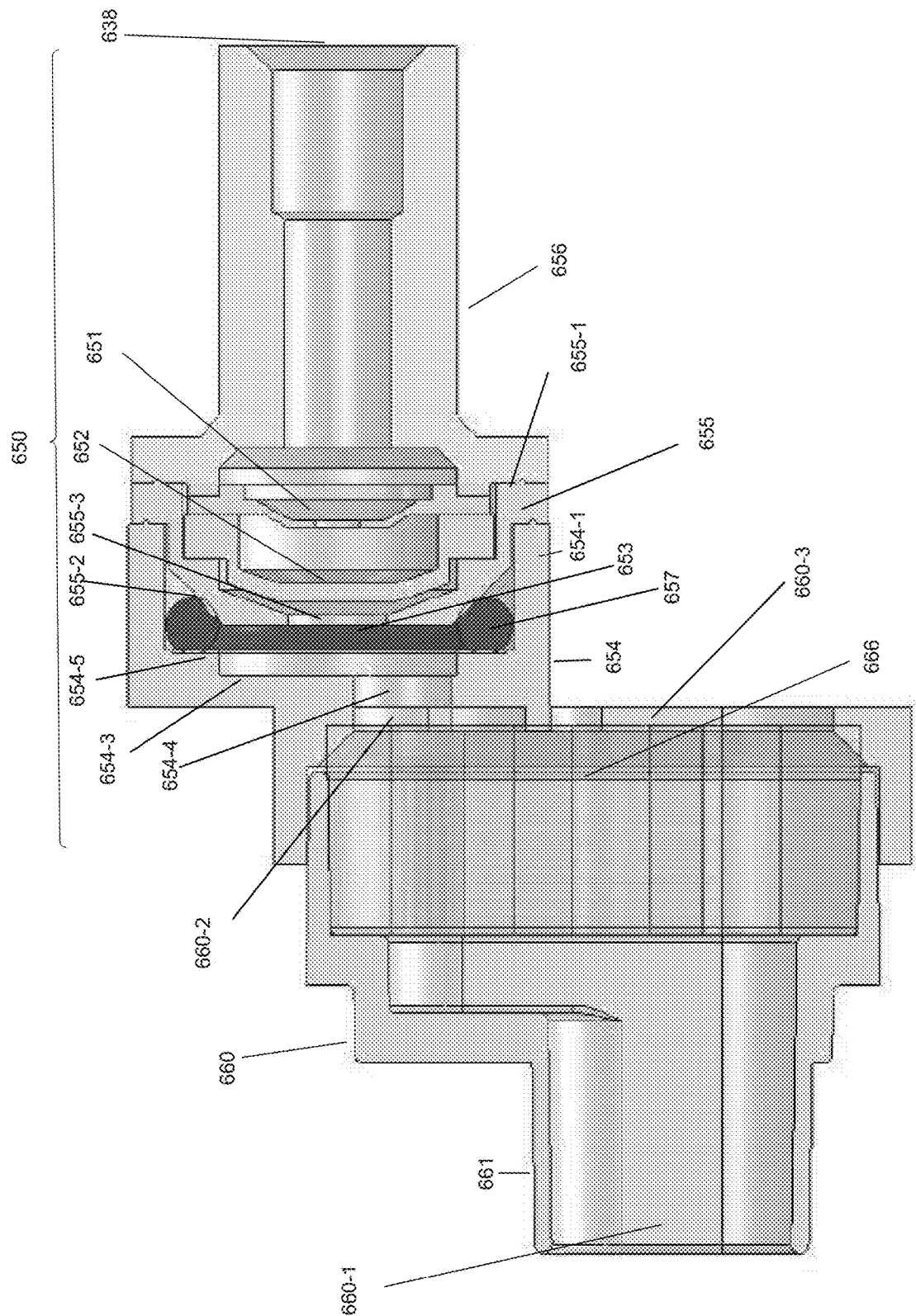
FIG. 6 is a cross sectional view of a manifold and a test port retainer suitable for use in the surgical apparatuses of FIGS. 1, 2A to 2D, and 3.

FIG. 6 is a cross sectional view of one aspect of a manifold 660 and a test port retainer 650. Manifold 660 is one example of manifold 360 and manifolds 260A to 260D. Test port retainer 650 is one example of test port retainers 250A to 250D and of test port retainer 350.

Test port retainer 650 connects pressure test port 638 to manifold 660. Test port retainer 650 includes a body 654, a seal retainer 655, and an end cap 656. A probe seal 651, a liquid exclusion barrier 652, and a hydrophobic membrane 653 are mounted within test port retainer 650 with probe seal 651 being closest to pressure test port 638 and hydrophobic membrane 653 being farthest from pressure test port 638. Hydrophobic membrane 653 is optional.

Body 654 includes an inner wall 654-3 with an opening 654-4 that is directly adjacent opening 660-2 of manifold 660 so that there is a bi-directional fluid communication path between test port retainer 650 and manifold 660. Within body 654, an O-ring 657 pushes against an outer circumferential portion of a first surface of hydrophobic membrane 653 to seat an outer circumferential portion of a second surface of hydrophobic membrane 653 against a step 654-5 that extends from wall 654-3 into the inner volume of body 654.

A second end 655-2 of seal retainer 655 includes an opening 655-3. A tapered surface of seal retainer 655 holds O-ring 657 against the outer circumferential portion of the first surface of hydrophobic membrane 653. A first end 655-1 of seal retainer 655 is positioned between first end 654-1 of body 654 and a second end of end cap 656 to form the outer surface of test port retainer 650. First end 655-1 forms a groove with the second end of end cap 656. Probe seal 651 and liquid exclusion barrier 652 are mounted in this groove.

Probe seal 651 has a circular opening in the center, in this aspect, and is designed to form a seal around a tip of a pressure test probe. Liquid exclusion barrier 652 is an x-slit valve, in one aspect. Hydrophobic membrane 653 is, in one aspect, a polyvinylidene difluoride (PVDF) membrane, as described above.

Probe seal 651 is an example of probe seals 251A to 251D and of probe seal 351. Liquid exclusion barrier 652 is an example of liquid exclusion barriers 252A to 252D and of liquid exclusion barrier 352. Hydrophobic membrane 653 is an example of hydrophobic membranes 253A to 253B and of hydrophobic membrane 353.

End cap 656, seal retainer 655, and body 654 are welded together to form a unitary body for test port retainer 650.

Manifold 660 includes three openings 660-1, 660-2, and 660-3. In one aspect, manifold 660 is made of a polymer formed by injection molding polyphenylsulfone (PPSU). Polyphenylsulfone is a heat and chemical-resistant. Polyphenylsulfone offers tensile strength up to 55 MPa (8000 psi). Thus, PPSU can withstand continuous exposure to moisture and high temperatures and absorb impact without cracking or breaking. One example of a polyphenylsulfone suitable for forming manifold 660 is medical grade Radel® R5500 resin. (Radel® is a U.S. registered trademark of Solvay Advanced Polymers L.L.C.)

First opening 660-1 in a flange 661 of manifold 660 communicates with a central lumen of a central tube, because the inner diameter of the central tube is sized so that the central tube can be force fit over the flange to form a pressure tight seal. A pressure seal 666 is mounted adjacent to third opening 660-3. A cable and light pipe (not shown) pass through pressure seal 666 and then through third opening 660-3. Pressure seal 666 is made from a two-part, platinum-catalyzed, heat-cured silicone elastomer. A two-part, platinum-catalyzed, heat-cured silicone elastomer suitable for use in making pressure seal 666 is sold by Dow Corning® under the tradename QP1-20 Liquid Silicone Rubber.

As explained more completely below, in assembly, light pipe 362 and pressure-sealed electrical cable 361 are passed through pressure seal 666 and then this assembly is mounted in manifold 660. Next, test port retainer 650 is mounted on an end of manifold 660 that includes pressure seal 666. In this aspect, the interface between test port retainer 650 and manifold 660 is stepped. Test port retainer 650 is secured to the end of manifold including pressure seal 666 so that manifold 660 exerts a radially inward force which compresses pressure seal 666 around light pipe 362 and pressure-sealed electrical cable 361 to form a pressure tight seal. As used herein, a pressure tight seal is a seal that allows the pressure chamber within the endoscope to maintain a predetermined minimum pressure that is required to pass a pressure test.

The following discussion applies to each of endoscopes 135-1, 235A, 235B, 235C, and 235D. Specifically, a description of an element with respect to FIGS. 7A to 7C, 8, and 9A to 9C with a name that is the same as a name of an element in endoscopes 135-1, 235A, 235B, 235C, and 235D applies to the element in endoscopes 135-1, 235A, 235B, 235C, and 235D with that name. Similarly, a description of an element with respect to endoscopes 135-1, 235A, 235B, 235C, and 235D with a name that is the same as a name of an element in FIGS. 7A to 7C, 8, and 9A to 9C applies to the element in FIGS. 7A to 7C, 8, and 9A to 9C with that name Thus, the correspondence between elements in the various drawings in not expressly called out in the following description to avoid distracting from the inventive aspects.

Typically, a prior art endoscope used in a computer-assisted teleoperated system included a single continuous electrical and illumination bundle. The electrical and illumination components in the bundle were separate. This bundle ran from an endoscopic imaging system to the housing of the endoscope, through the housing of the endoscope, and down the shaft of the endoscope to the distal end of the shaft. The electrical and illumination components followed different paths through the shaft to the distal end of the shaft. This endoscope was assembled in a proximal to a distal direction.

In contrast, instead of one single continuous electrical and illumination bundle that is threaded through the endoscope from an endoscopic imaging system remote from the endoscope, the endoscope is divided into multiple testable subassemblies that are integrated together in assembling the endoscope. FIGS. 7A to 7C illustrate examples of three subassemblies 701, 702, 703.

One subassembly is a central tube bundle subassembly 701 (FIG. 7A), sometimes referred to as central tube bundle 701 and as a third subassembly. Central tube bundle 701 includes a central tube 765, an image capture subassembly 742 (sometimes referred to as a second subassembly), pressure-sealed electrical cable 361, and light pipe 362. In one aspect, central tube 765 is a single continuous tube with a single central lumen. In another aspect, central tube 765 is a molded single continuous silicone tube with a single central lumen. The single continuous tube eliminates potential leak paths Image capture subassembly 742 is equivalent to the image capture assemblies described above.

Central tube 765 is connected to image capture subassembly 742 so that a pressure tight seal is formed between central tube 765 and image capture subassembly 742. Pressure-sealed electrical cable 361 is electrically connected to an image capture unit within image capture subassembly 742. Ends 501-1 and 501-2 of fiber optic bundle 501 are terminated in image capture subassembly 742 to output light through a distal end of image capture subassembly 742. Pressure-sealed electrical cable 361 and light pipe 362 are routed through a central lumen of central tube 762.

As explained more completely below, in one aspect, cable 361 and the image capture unit are assembled as a subassembly. The image capture unit of this subassembly is inserted in a shell with cable 361 extending through a proximal end of the shell in a proximal direction. The distal end of light pipe 362 is mounted in the shell with light pipe 362 also extending through the proximal end of the shell in the proximal direction. A lid is affixed to the distal end of the shell and this sub-assembly is subjected to a seal verification test. Cable 361 and light pipe 362 are then threaded through the lumen of central tube 765 and central tube is affixed to the shell to form central tube bundle subassembly 701. Central tube bundle subassembly 701 can be tested to determine whether the camera or cameras in the image capture unit are working properly and whether the light pipe is providing the proper illumination.

Another subassembly is base instrument subassembly 702 (FIG. 7B), sometime referred to as a fourth subassembly. Base instrument subassembly 702 includes a base, a shaft, a parallel motion mechanism 770, and a wrist joint assembly 780, in this aspect. Parallel motion mechanism 770 and wrist joint assembly 780 are each an example of an articulating assembly. Other articulating assemblies could be used in base instrument subassembly 702, or alternatively base instrument subassembly 702 may not contain an articulating assembly (see FIGS. 2B and 2D), or may contain only one articulating assembly, e.g., wrist joint assembly 780.

Base instrument subassembly 702 includes a repeater board, a manifold such as manifold 660, and a test port retainer such as test port retainer 350, and a cable subassembly connector 705. Base instrument subassembly 702 is connected to a proximal end of shaft 757. The repeater board includes a laser on indicator, e.g., one or more light emitting diodes, a voltage regulator, a first connector configured to connect to the proximal end of pressure-sealed electrical cable 361 and a second connector configured to electrically connect to instrument-to-endoscopic imaging system cable subassembly 703. The repeater board receives power and control signals from instrument-to-endoscopic imaging system cable subassembly 703 (FIG. 7C) and provides these to image capture subassembly 742. The repeater board receives video signals from image capture subassembly 742 and provides these video signals to instrument-to-endoscopic imaging system cable subassembly 703.

A distal end of shaft 757 is connected to a proximal end of a parallel motion mechanism 770. The distal end of parallel motion mechanism 770 is connected to a proximal end of a wrist assembly 780.

A wrist joint assembly suitable for use as wrist joint assembly 780 is described, for example, in U.S. Patent Application No. US 2003/0036748 A1 (filed Jun. 28, 2002 disclosing "Surgical Tool Having Positively Positionable Tendon-Activated Multi-Disk Wrist Joint"), which is incorporated herein by reference. A parallel motion mechanism suitable for use as parallel motion mechanism 770 is described, for example, in U.S. Pat. No. 7,942,868 B2 (filed Jun. 13, 2007, disclosing "Surgical Instrument With Parallel Motion Mechanism"), which also is incorporated herein by reference. Parallel motion mechanism 770 and wrist joint assembly 780 are built and the cables are tensioned in the same way as in the prior art, with the exception, in one aspect, of the most distal disk of wrist joint assembly 780, as described below with respect to FIG. 10B.

In one aspect, a range of motion of parallel motion mechanism 770 and wrist joint assembly 780 are tested. Also, cable friction through shaft 737 and friction within parallel motion mechanism 770 and wrist joint assembly 780 are tested.

After testing of subassemblies 701 and 702, central tube bundle 701 is routed from the distal end of shaft 737 to the proximal end of shaft 737. Pressure-sealed electrical cable 361 and light pipe 362 are routed through manifold 660 and pressure-sealed electrical cable 361 is connected to the repeater board. The distal end of central tube 765 is affixed to manifold 660 and image capture subassembly 742 is affixed to wrist joint assembly 780. After the combining of subassemblies 701 and 702, the electrical, illumination, and camera tests can be repeated to assure that nothing was damaged during the assembly process.

To complete the assembly for testing, yet another subassembly, an instrument-to-endoscopic imaging system cable subassembly 703 (FIG. 7C), which is an example of a fifth subassembly, is connected to base instrument subassembly 702. The test can now be repeated using an instrument-to-endoscopic imaging system cable subassembly 703 to determine whether the system is functioning properly.

Figure 8:
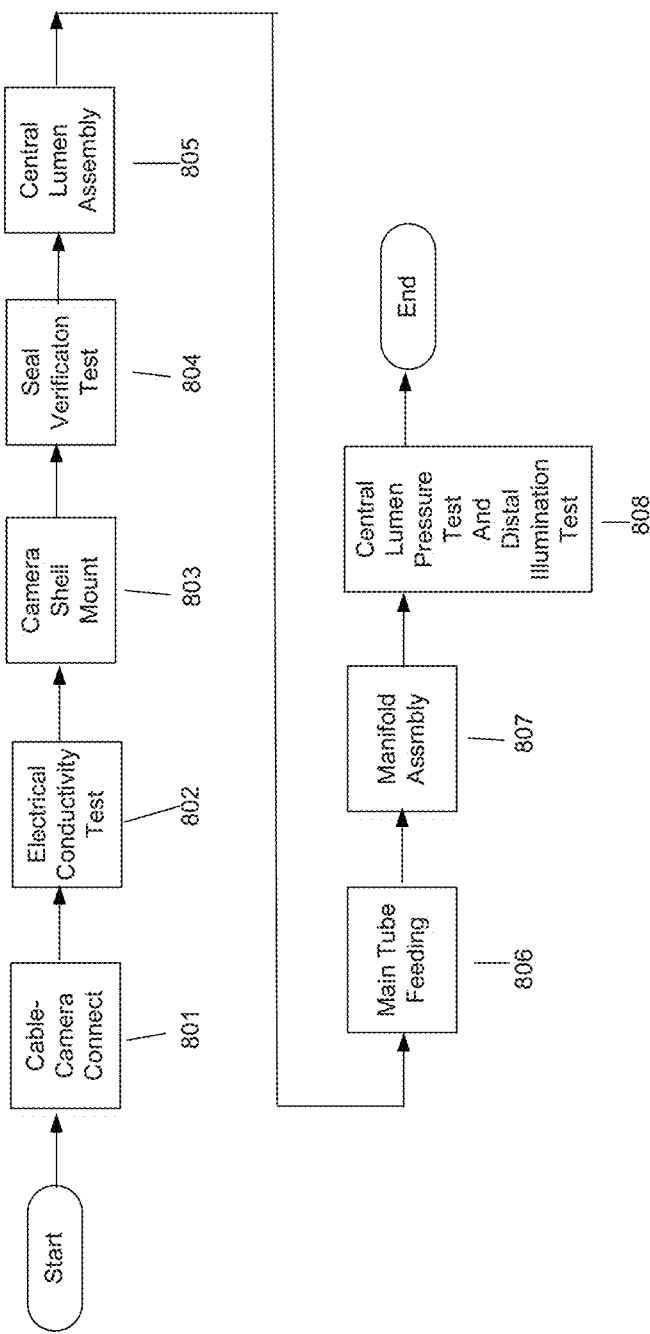
FIG. 8 is a process flow diagram for assembling and testing subassemblies in the assembly of an endoscope.
Figure 9A:
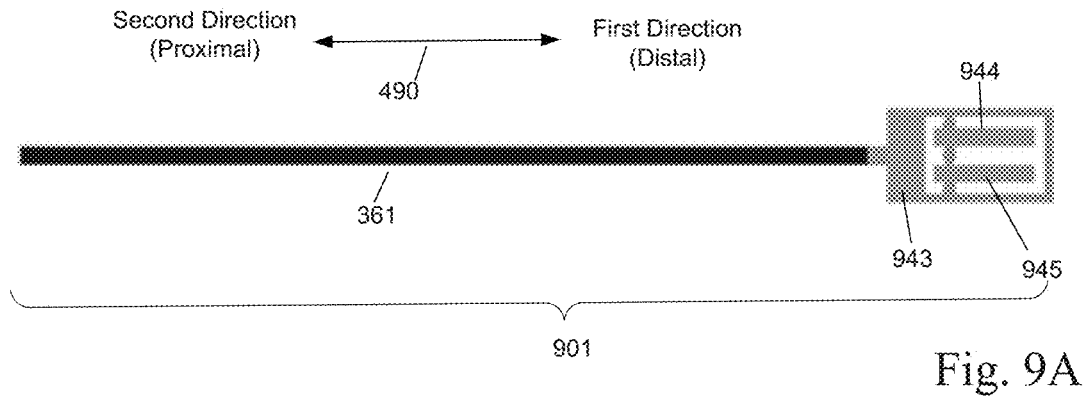
FIGS. 9A to 9C illustrate subassemblies used in the process of FIG. 8.

FIG. 8 is a process flow diagram for assembling and testing subassemblies of an endoscope during assembly of the endoscope. In CABLE-CAMERA CONNECT process 801, each of plurality of conductors 410 in a distal end of pressure-sealed electrical cable 361 is connected to a corresponding conductor in an image capture unit 943 (FIG. 9A). In this aspect, connector 425 on the distal end of pressure-sealed electrical cable 361 is connected to a connector on image capture unit 943. In this example, image capture unit 943 is a stereoscopic image capture unit, and so includes two stereoscopic cameras 944, 945. The use of stereoscopic cameras is optional, because the assembly and testing process is the same if only a single camera is used. For a single camera, there may be a different number of conductors in plurality of conductors 410 in pressure-sealed electrical cable 361.

A ground wire is woven into outer braided shield 412 of pressure-sealed electrical cable 361, and then outer braided shield 412 is electrically connected to the body of image capture unit 943. The ground wire is electrically attached to a ground crimp that grounds stereoscopic cameras 944, 945. The completed electrical-cable and image-capture-unit subassembly 901, an example of a first subassembly, is illustrated in FIG. 9A.

Upon completion of CABLE-CAMERA CONNECT process 801, the electrical-cable and image-capture-unit subassembly 901 is tested in ELECTRICAL CONDUCTIVITY TEST process 802, sometimes referred to as process 802. In process 802, the electrical conductivity of electrical-cable and image-capture-unit subassembly 901 is checked by powering stereoscopic cameras 944, 945 and observing and checking the video feed from stereoscopic cameras 944, 945.

Figure 9B:
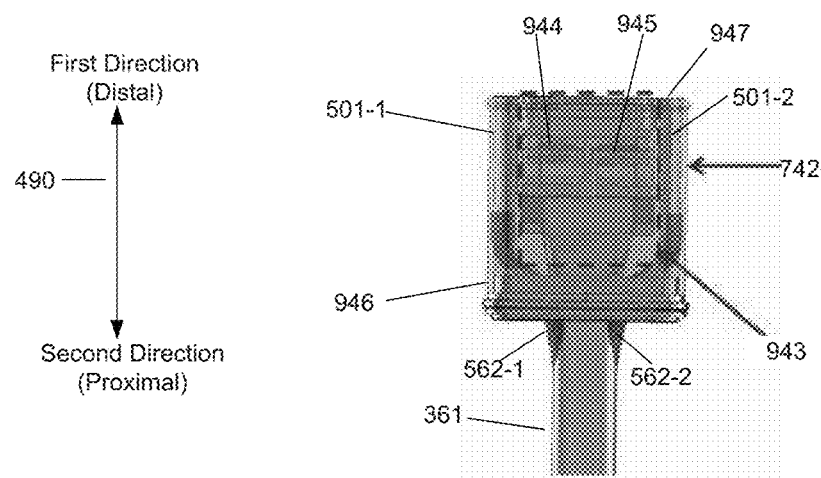

Upon successful completion of ELECTRICAL CONDUCTIVITY TEST process 802, image capture subassembly 742 is assembled in CAMERA SHELL MOUNT process 803, sometimes referred as process 803. In process 803, prior to mounting electrical-cable and image-capture-unit subassembly 901 in a shell 946, the distal ends of light pipes 562-1 and 562-2 are potted directly into enclosures in the interior of shell 946. Then, electrical-cable and image-capture-unit subassembly 901 is loaded from the distal end of shell 946 and arranged so that light pipes 562-1 and 562-2 are on either side of image capture unit 943, as illustrated in FIG. 9B. Pressure-sealed electrical cable 361 extends in a proximal direction from the proximal end of shell 946 as do light pipes 562-1 and 562-2. In FIG. 9B, a side of shell 946 is removed so that light pipes 562-1 and 562-2 and image capture unit 943 are visible. Finally, a lid 947 is welded to the distal end of shell 946 to form a sealed image capture subassembly 742, sometimes referred to as a second subassembly. Lid 947 includes windows for each of the cameras and each of the light pipes.

Upon completion of CAMERA SHELL MOUNT process 803, a pressure test is performed to verify through pressure decay that the weld between lid 947 and shell 946 is water tight in SEAL VERIFICATION TEST process 804. In one aspect, the pressure testing is accomplished by creating a pressure differential between the inside and the outside of the shell (including image capture unit 943 and light pipe ends 562-1 and 562-2), and measuring the decay in the pressure. The orientation of the pressure differential does not matter.

Following successful conclusion of SEAL VERIFICATION TEST process 804, CENTRAL LUMAN ASSEMBLY process 805, sometimes referred to as process 805, is performed. Prior to considering process 805, central tube 765 is further described. As explained above, in one aspect, central tube 765 is a molded single continuous silicone tube with a single central lumen. In one aspect, central tube 765 is made of an injection molded hollow cylindrical tube that in turn is injection molded to a tapered oval shaped tube.

In one aspect, central tube 765 is made from medical grade silicone elastomers. Initially, a proximal cylindrical tube portion central tube 765 is formed using a two-component, enhanced-tear-resistant (ETR) silicone elastomer that consists of dimethyl and methylvinyl siloxane copolymers and reinforcing silica. Equal portions (by weight) of the two-components are thoroughly blended together prior to injection molding. The elastomer is thermally cured via addition-cure (platinum-cure) chemistry. A two-component, enhanced-tear-resistant silicone elastomer is provided by Dow Corning under the trade name SILASTIC® BioMedical Grade ETR Elastomer Q7-4780. (SILASTIC is a U.S. registered trademark of Dow Corning Corporation.

Next, the proximal cylindrical tube portion of central tube 765 is molded to a distal portion of central tube 765. The distal portion of central tube 765 is a molded transition between the distal end that fits around image capture assembly flange 966 and the proximal cylindrical tube portion of central tube 765, The distal portion of central tube 765 is made using two-part platinum-catalyzed silicone elastomers. The two parts in equal portions (by weight) are thoroughly blended together prior to injection molding. The elastomer is thermally cured via an addition-cure (platinum-catalyzed) reaction. When blended and cured, the resulting elastomer consists of crosslinked dimethyl and methyl-vinyl siloxane copolymers and reinforcing silica. The elastomer is heat stable up to 204° C. (400° F.) and can be autoclaved. A two-part platinum-catalyzed silicone elastomer is provided by Dow Corning under the trade name SILASTIC® Bio-Medical Grade Liquid Silicone Rubber Q7-4850.

In one aspect, both the inner wall and the outer wall of central tube 765 are coated with an anti-friction coating. One suitable anti-friction coating is a Parylene-N coating. In this aspect, outer insulating jacket 403 of pressure-sealed electrical cable 361 is a silicone jacket coated with an anti-friction coating such as a Parylene-N coating. In one aspect, all of insulating jackets in pressure-sealed electrical cable 361 are coated with the anti-friction coating. Similarly, the outer surface of protective sheath 502 including protective sheath 502-1 of first end 562-1 of light pipe 362 and protective sheath 502-2 of second end 562-2 of light pipe 362 is a silicone sheath coated with an anti-friction coating such as a Parylene-N coating.

Initially, image capture assembly flange 966 (FIG. 9C) is mounted in a distal end of central tube 765 in process 805. As explained above, the perimeter of the distal end of central lumen is slightly smaller than the outer perimeter of flange 966 so that when central tube 765 is forced on flange 966 a pressure tight seal is formed. In one aspect, a piece of heat shrink tubing is shrunk around the outer perimeter of the distal end of central tube 765 to further assure that a pressure tight seal is formed between central tube 765 and flange 966.

Figure 9C:
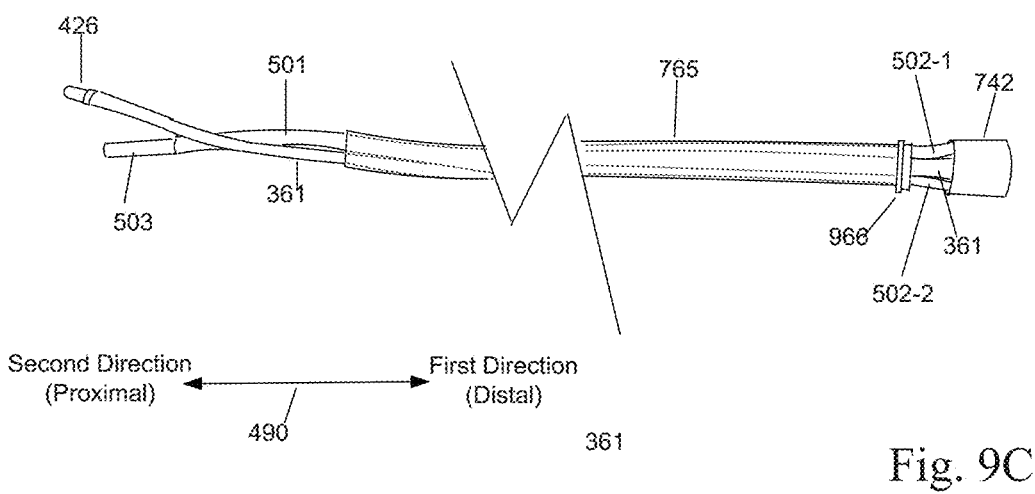

Next, pressure-sealed electrical cable 361 and light pipe 362 are threaded through flange 966 and central tube 765 to obtain the structure illustrated in FIG. 9C. The antifriction coatings on the wall of the central lumen of central tube 765, on outer insulating jacket 403 of pressure-sealed electrical cable 361, and on the outer surface of sheath 502 of light pipe 362 facilitates the stringing of pressure-sealed electrical cable 361 and light pipe 362 through central tube 765 without the use of force that might damage either one or both of pressure-sealed electrical cable 361 and light pipe 362. Flange 966 is welded to a proximal end of image capture subassembly 742 to obtain central tube bundle subassembly 701, sometimes referred to as a third subassembly.

Following completion of CENTRAL LUMAN ASSEMBLY process 805, MAIN TUBE FEEDING process 806, sometimes referred to as process 806, is performed. In process 806, central tube bundle 701 is feed through wrist joint assembly 780, parallel motion mechanism 770, and shaft 737 so that the proximal end of central tube bundle 701 emerges from the proximal end of shaft 737. The anti-friction coating on the outer surface of central tube 765 facilitates the feeding of central tube bundle into base instrument subassembly 702 from the distal end of base instrument subassembly 702. A lengthwise axis of central tube 765 is coincident with a lengthwise axis of shaft 737, parallel motion mechanism 770, and wrist joint assembly 780, in this example.

Following completion of MAIN TUBE FEEDING process 806, MANIFOLD ASSEMBLY process 807, sometimes referred to as process 807, is performed. In process 807, a piece of heat shrink tubing is slid over the proximal end of central tube 765 and then the proximal ends of pressure-sealed electrical cable 361 and of light pipe 362 are threaded through opening 660-1 in flange 661 of manifold 660. Next, the proximal ends of pressure-sealed electrical cable 361 and of light pipe 362 are threaded through the corresponding channels in pressure seal 666 and pressure seal 666 is mounted in the end of manifold 660 opposite to flange 661. Test port retainer 650 is mounted on manifold 660 and screws are used to tighten test port retainer around manifold 660 so that manifold 660 compresses pressure seal 666 around pressure-sealed electrical cable 361 and around light pipe 362 to form a pressure tight seal.

The circumference of the proximal end of central lumen is slightly smaller than the outer circumference of flange 661 so that when the proximal end central tube 765 is forced on flange 661 a pressure tight seal is formed. In one aspect, the piece of heat shrink tubing is shrunk around the outer circumference of the proximal end of central tube 765 to further assure that a pressure tight seal is formed between central tube 765 and flange 661.

Finally, to complete process 807, the proximal ends of pressure-sealed electrical cable 361 are connected to the repeater board in base instrument subassembly 702. Following completion of, MANIFOLD ASSEMBLY process 807, sometimes referred to as process 807, CENTRAL LUMEN PRESSURE TEST AND DISTAL ILLUMINATION TEST process 808 is performed.

Prior to considering CENTRAL LUMEN PRESSURE TEST AND DISTAL ILLUMINATION TEST process 808, the rationale for the pressure test is considered. Detection of a breach large enough to pass blood into the pressure chamber of the endoscope when pressurized at insufflation pressure, approximately 15 mmHg, is needed for patient safety. Due to surface tension, there will be some minimum hole size, below which insufflation pressure is not be able to force blood through the breach. However, air flow through the breach occurs at some level, regardless of the hole size. Therefore, the method of assuring that there is not a breach large enough to pass blood as insufflation pressures is to pressurize the pressure chamber in the endoscope to a predetermined pressure, such as 150 mmHg, and to observe whether pressure falls below a predefined minimum pressure during a predetermined time interval. If the pressure does not fall below the predefined minimum pressure at the end of the predetermined time interval, the endoscope is deemed not to have a breach that would pass blood into the pressure chamber volume when pressurized at insufflation pressure. This is a worst case assessment, as the pressure test interrogates all breaches, including those too small to allow blood to pass. The details of the pressure test are determined empirically by assessing the leak rates of different breaches and their corresponding blood flow properties.

In CENTRAL LUMEN PRESSURE TEST AND DISTAL ILLUMINATION TEST process 808, a test probe is inserted in the pressure test port of the endoscope, and the pressure test chamber, as defined above, is pressurized to a predetermined pressure, e.g. 150 mmHG. If the pressure test chamber holds the pressure to greater than a predetermined minimum pressure, e.g., 40 mmHg, for a predetermined time interval, e.g., 30 seconds, there are no fluid pathways at insufflation pressure for communication between the environment outside endoscope and the interior of pressure test chamber that are of significance during a surgical procedure. Consequently, pressure test chamber cannot be contaminated during a surgical procedure in which the endoscope is used at insufflation pressure. In the illumination test, properties such as optical transmission of the light pipe and the number of unbroken illumination fibers are measured.

In one aspect, a distal disk 1081 (FIG. 10A) of wrist joint assembly 780 is welded to the proximal end of image capture subassembly 742 after MAIN TUBE FEEDING PROCESS 806. A plurality of wrist actuation cables are connected to distal disk 1081. One actuation cable 1082 of the plurality of wrist actuation cables is shown in the cutaway diagram of FIG. 10A. Actuation cable 1082 enters distal disk 1081 from a through hole in a proximal end surface of distal disk 1081 and extends into a slot 1081A. A crimp fitting 1083, which is an example of a cable end fitting, on the distal end of actuation cable 1082 is positioned in slot 1081A in distal disk 1081 of wrist joint assembly 780. (A cable end fitting is sometimes referred to as a fitting.) Slot 1081A extends in the proximal direction into distal disk 1081 from a distal end surface of distal disk 1081. To block a potential leak path from the distal end of slot 1081A proximally around crimp fitting 1083 and around cable 1082 to the outside environment, in this aspect, slot 1081A is filled from the distal end with a room temperature vulcanization silicone to encapsulate crimp fitting 1083 and to fill the open volume of slot 1081A.

In another aspect, the need for filling slot 1081A and encapsulating crimp fitting 1083 is eliminated. In this aspect, distal disk 1081 is split into two distal disks 1081-1 and 1081-2 of wrist joint assembly 780. Disk 1081-2 is referred to as second distal disk 1081-2 because it is the second disk from the distal end of wrist joint assembly 780. Disk 1081-1 is referred to as first distal disk 1081-1 because it is the first disk at the distal end of wrist joint assembly 780.

A plurality of wrist actuation cables for wrist joint assembly 780 are connected to the mated combination of first distal disk 1081-1 and second distal disk 1081-2. One actuation cable 1082 of the plurality of wrist actuation cables is shown in the cutaway diagram of FIG. 10B.

Actuation cable 1082 pass through a through hole extending from a proximal end surface of second distal disk 1081-2 to a distal surface of second distal disk 1081-2. Actuation cable 1082 extends into a slot 1081B in first distal disk 1081-1. A crimp fitting 1083 on the distal end of actuation cable 1082 is positioned in slot 1081B in first distal disk 1081-1 of wrist joint assembly 780. Slot 1081A extends in the distal direction into first distal disk 1081-1 from a proximal end surface of first distal disk 1081.

Outer circumferential distal end surface 1081-1DS of first distal disk 1081-1 is welded to the shell of image capture subassembly 742. An outer circumferential edge distal edge surface 1081-2DS of second distal disk 1081-2 is welded to outer circumferential proximal edge surface 1081-1PS of first distal disk 1081-1. There is no longer a leak path around crimp fitting 1083 and around cable 1082 to the outside environment because first distal disk 1081-1 blocks any leak path to the volume inside the pressure chamber. Crimp fitting 1083 is encapsulating in a volume created by the mating of first distal disk 1081-1 to second distal disk 1081-2 and there is no path of significance during a surgical procedure between the pressure test chamber and the volume created by the mating of first distal disk 1081-1 to second distal disk 1081-2.

Thus, as illustrated in FIG. 10B, an articulating assembly includes a first disk 1081-1, a second disk 1081-2, an actuation cable 1082 having a distal end, and a crimp fitting 1083. Actuation cable 1082 passes through second disk 1081-2, and crimp fitting 1083 is attached to the distal end of actuation cable 1082. Crimp fitting 1083 is contained in a cavity formed by mating of first disk 1081-1 to second disk 1081-2.

As used herein, "first," "second," "third," "fourth," etc. are adjectives used to distinguish between different components or elements. Thus, "first," "second," "third," "fourth," etc. is not intended to imply any ordering of the components or elements or any particular number of components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. An endoscope comprising:
   a pressure-sealed electrical cable connected to an image capture unit;
   a shell having a distal end and a proximal end, the image capture unit being mounted in the shell, the pressure-sealed electrical cable extending proximally through the proximal end of the shell;
   a manifold with a plurality of openings, wherein a first of the plurality of openings is in communication with the shell, wherein a second of the plurality of openings is in communication with a connector, wherein a third of the plurality of openings is in communication with a pressure test port, wherein the pressure-sealed electrical cable passes through the first and second of the plurality of openings and is connected to the connector; and
   a pressure tight seal in the second or the first and the second of the plurality of openings and formed around the pressure-sealed electrical cable, wherein the pressure-sealed electrical cable comprises a structure to prevent a through path for gas flow within the pressure-sealed electrical cable.

2. The endoscope of claim 1, further comprising:
   a light pipe having a distal end, the distal end of the light pipe being mounted in the shell, and the light pipe extending proximally through the proximal end of the shell.

3. The endoscope of claim 1, wherein the pressure-sealed electrical cable further comprises:
   one or more conductors, each of the one or more conductors having an insulating jacket;
   a first shield surrounding the one or more conductors;
   a second insulating jacket surrounding the first shield; and
   a first pressure seal formed in and around the first shield.

4. The endoscope of claim 3, the pressure-sealed electrical cable further comprising;
   a second shield surrounding the second insulating jacket;
   a third insulating jacket surrounding the second shield; and
   a second pressure seal formed around and in the second shield and extending between the second insulating jacket and the third insulating jacket.

5. The endoscope of claim 4, the pressure-sealed electrical cable having a first end and a second end, the first pressure seal being adjacent one of the first end and the second end, and the second pressure seal being adjacent another of the first end and the second end.

6. A medical instrument comprising:
   an assembly, wherein a first electronic unit is positioned within the assembly;
   a housing coupled to the assembly via a pressure tight seal at a first opening of the housing, wherein a second opening of the housing is in communication with a second electronic unit, and wherein a third opening of the housing is in communication with a pressure test port; and
   a pressure-sealed electrical cable comprising one or more conductors and having a proximal end and a distal end, the proximal end of the pressure-sealed electrical cable coupled to the second electronic unit and the distal end of the pressure-sealed electrical cable coupled to the first electronic unit, wherein the pressure-sealed electrical cable passes through the first and the second opening of the housing,
   wherein the pressure-sealed electrical cable passes through the pressure tight seal and comprises a structure to prevent a through path for gas flow within the pressure-sealed electrical cable between the assembly and the housing, wherein the pressure tight seal is in the first opening of the housing and formed around the pressure-sealed electrical cable, wherein a second pressure tight seal is in the second opening of the housing and formed around the pressure-sealed electrical cable, wherein each of the structure, the pressure tight seal and the second pressure tight seal are sufficient to maintain a pressure during a pressure test of the medical instrument via the pressure test port.

7. The medical instrument of claim 6, further comprising:
   a tube having a proximal end and a distal end, wherein the distal end of the tube is coupled to the assembly, and the proximal end of the tube is coupled to the housing by the pressure tight seal.

8. The medical instrument of claim 7, wherein the assembly comprises:
- a shell having a distal end and a proximal end, the first electronic unit being mounted in the shell, the pressure-sealed electrical cable extending proximally through the proximal end of the shell; and
- a lid affixed to the distal end of the shell.

9. The medical instrument of claim 8, wherein the first electronic unit is a camera.

10. The medical instrument of claim 9, further comprising:
- a light pipe having a distal end, the distal end of the light pipe being mounted in the shell, and the light pipe extending proximally through the proximal end of the shell.

11. The medical instrument of claim 6, wherein the pressure-sealed electrical cable comprises a first shield surrounding the one or more conductors and an insulating jacket surrounding the first shield, wherein the structure comprises a first pressure seal formed in and around the first shield.

12. The medical instrument of claim 11, wherein the pressure-sealed electrical cable further comprises:
- a second shield surrounding the insulating jacket;
- a second insulating jacket surrounding the second shield; and
- a second pressure seal formed in and around the second shield and extending between the second insulating jacket and a third insulating jacket.

13. A surgical apparatus comprising a pressure-sealed electrical cable, the pressure-sealed electrical cable further comprising:
- one or more conductors, each of the one or more conductors individually has an insulating jacket;
- a first shield surrounding the one or more conductors;
- a second insulating jacket surrounding the first shield; and
- a first pressure seal formed in and around the first shield and around the one or more conductors and extending between the second insulating jacket and the insulating jacket of the one or more conductors,
- wherein the second insulating jacket does not extend a full length of the pressure-sealed electrical cable exposing a first edge of the first shield and a second edge of the first shield, and the first pressure seal is formed in and around the first shield by heat shrink tubing affixed to the first insulating jacket adjacent to the first edge and the second edge, and
- wherein silicon is injected into the heat shrink tubing so that a shrinking of the heat shrink tubing forces the silicon into any openings of the first shield and into any openings between the one or more conductors to form the first pressure seal.

14. The surgical apparatus of claim 13, the pressure-sealed electrical cable further comprising;
- a second shield surrounding the second insulating jacket;
- a third insulating jacket surrounding the second shield; and
- a second pressure seal formed around and in the second shield and extending between the second insulating jacket and the third insulating jacket.

15. The surgical apparatus of claim 14, the pressure-sealed electrical cable having a first end and a second end, the first pressure seal being adjacent one of the first end and the second end, and the second pressure seal being adjacent another of the first end and the second end.

16. The endoscope of claim 1, wherein the pressure-sealed electrical cable is a shielded cable with a shield that surrounds one or more conductors, wherein the structure is a seal formed in and around the shield that is sufficient to maintain a minimum pressure required during a pressure test of the endoscope,
- wherein the pressure-sealed electrical cable has an insulating jacket surrounding the shield,
- wherein the insulating jacket does not extend a full length of the pressure-sealed electrical cable exposing a first edge of the shield and a second edge of the shield, and the seal is formed in and around the shield by heat shrink tubing affixed to the insulating jacket adjacent to the first edge and the second edge, and
- wherein silicon is injected into the heat shrink tubing so that a shrinking of the heat shrink tubing forces the silicon into any openings of the shield to form the seal.

17. The medical instrument of claim 6, wherein the pressure-sealed electrical cable is a shielded cable with a shield that surrounds one or more conductors, wherein the structure is a seal formed in and around the shield that is sufficient to maintain a minimum pressure required during a pressure test of the medical instrument,
- wherein the pressure-sealed electrical cable has an insulating jacket surrounding the shield,
- wherein the insulating jacket does not extend a full length of the pressure-sealed electrical cable exposing a first edge of the shield and a second edge of the shield, and the seal is formed in and around the shield by heat shrink tubing affixed to the insulating jacket adjacent to the first edge and the second edge, and
- wherein silicon is injected into the heat shrink tubing so that a shrinking of the heat shrink tubing forces the silicon into any openings of the shield to form the seal.

* * * * *